US009771616B2

(12) United States Patent
Bogdanova et al.

(10) Patent No.: US 9,771,616 B2
(45) Date of Patent: Sep. 26, 2017

(54) GENETIC VARIANT OF THE ANNEXIN A5 GENE

(75) Inventors: Nadja Bogdanova, Münster (DE); Arseni Markoff, Münster (DE); Jürgen Horst, Münster (DE); Volker Gerke, Altenberge (DE)

(73) Assignee: Universitätsklinikum Münster, Münster (DE)

( * ) Notice: Subject to any disclaimer, the term of this patent is extended or adjusted under 35 U.S.C. 154(b) by 48 days.

(21) Appl. No.: 13/350,372

(22) Filed: Jan. 13, 2012

(65) Prior Publication Data
US 2012/0178156 A1 Jul. 12, 2012

Related U.S. Application Data

(62) Division of application No. 11/719,732, filed as application No. PCT/EP2005/012259 on Nov. 15, 2005, now Pat. No. 8,119,341.

(30) Foreign Application Priority Data

Nov. 19, 2004 (EP) .................................... 04027526

(51) Int. Cl.
*C07H 21/02* (2006.01)
*C07H 21/04* (2006.01)
*C12Q 1/68* (2006.01)
*C07K 14/47* (2006.01)

(52) U.S. Cl.
CPC ........ *C12Q 1/6883* (2013.01); *C07K 14/4721* (2013.01); *C12Q 1/6897* (2013.01); *C12Q 2600/136* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS 5,744,305 A 4/1998 Fodor et al.
5,837,832 A 11/1998 Chee et al.
6,582,908 B2 * 6/2003 Fodor et al. .................. 506/9

FOREIGN PATENT DOCUMENTS

WO WO 02/097114 12/2002

OTHER PUBLICATIONS

NEB catalog (1998/1999), pp. 121, 284.*
U01681 (NLM, NCBI, 1997).*
Fernandez et al; Gene, vol. 149, pp. 253-260; 1994.*
Rothstein et al; PNAS USA 1994, vol. 91, pp. 4155-4159.*
Genbank Accession No. U01681.1, NLM; NCBI (1997).

Bogdanova, K., et al. (2007) *A common haplotype of the annexin A5 (ANXA5) gene promoter is associated with recurrent pregnancy loss*, Human Molecular Genetics 16: 573-578.
Lucentini, J., (2004) *Gene Association Studies Typically Wrong*, The Scientist 24: 20.
Jüppner, H., (1995) *Functional Properties of the PTH/PTHrP Receptor*, Bone 17: 39S-42S.
Hegele, R.A., (2002) *SNP Judgments and Freedom of Associate*, Arterioscelerosis, Thrombosis, and Vascular Biology 22: 1058-1061.
PCT Search Report for International Application No. PCT/EP2005/012259; dated Apr. 6, 2006.
XP002371761, (2001) *602505792F1 NIH_MGC_77 Homo Sapiens cDNA clone Image: 4618183 5', mRNA sequence*, Database Accession No. BG484620.
Gerke, V. and Moss, S., (2002) *Annexins: From Structure to Function*, Physiological Review 82: 331-371.
Hayes, M. and Moss, S., (2004) *Annexins and disease*, Biochemical and Biophysical Research Communications 322: 1166-1170.
Rand, J., (2000) *The Pathogenic Role of Annexin-V in the Antiphospholipid Syndrome*, Current Rheumatology Reports 2: 246-251.
Carcedo, M., et al. (2001) *Functional analysis of the human annexin A5 gene promoter: a downstream DNA element and an upstream long terminal repeat regulate transcription*, Biochem. J. 356: 571-579.
Cookson, B., et al. (1994) *Organization of the Human Annexin V (ANX5) Gene*, Genomics 20: 463-467.
Creutz, C., (1992) *The Annexins and Exocytosis*, Science 258: 924-931.
Empson M., et al. (2002) *Recurrent Pregnancy Loss with Antiphospholipid Antibody: A Systematic Review of Therapeutic Trials*, The American College of Obstreticians and Gynecologists 99: 135-144.
Gonzalez-Conejero, R., et al., (2002) *A common polymorphism in the annexin V Kozak sequence (-1C>T) increases translation efficiency and plasma levels of annexin V, and decreases the risk of myocardial infarction in young patients*, Blood 100: 2081-2086.
Key, N. and McGlennen R., (2002) *Hyperhomocyst(e)inemia and Thrombophilia*, Arch Pathol Lab Med 126: 1367-1375.
Kozak, M. (2003) *Not every polymorphism close to the AUG codon can be explained by invoking context effects on initiation of translation*, Blood 101: 1202-1203.

(Continued)

*Primary Examiner* — Jehanne Sitton
(74) *Attorney, Agent, or Firm* — Kagen Binder, PLLC

(57) ABSTRACT

The present invention relates to a nucleic acid molecule comprising an annexin A5 (ANXA5) gene regulation element which comprises at least one point mutation corresponding to nucleotide 186 (G to A), 203 (A to C), 229 (T to C), and 276 (G to A) of SEQ ID NO: 2, a vector comprising the nucleic acid molecule, and a host transformed with the vector. The invention also relates to specific uses, in particular diagnostic uses of the nucleic acid molecules described herein. The invention also relates to haplotyping an ANXA5 gene regulation element from a nucleic acid from an individual which involves determining nucleotides present at positions 186, 203, 229 and 276 of the individual's copy of the ANXA5 gene regulation element by comparison to SEQ ID NO: 2.

23 Claims, 4 Drawing Sheets

(56) References Cited

OTHER PUBLICATIONS

Figure 1:
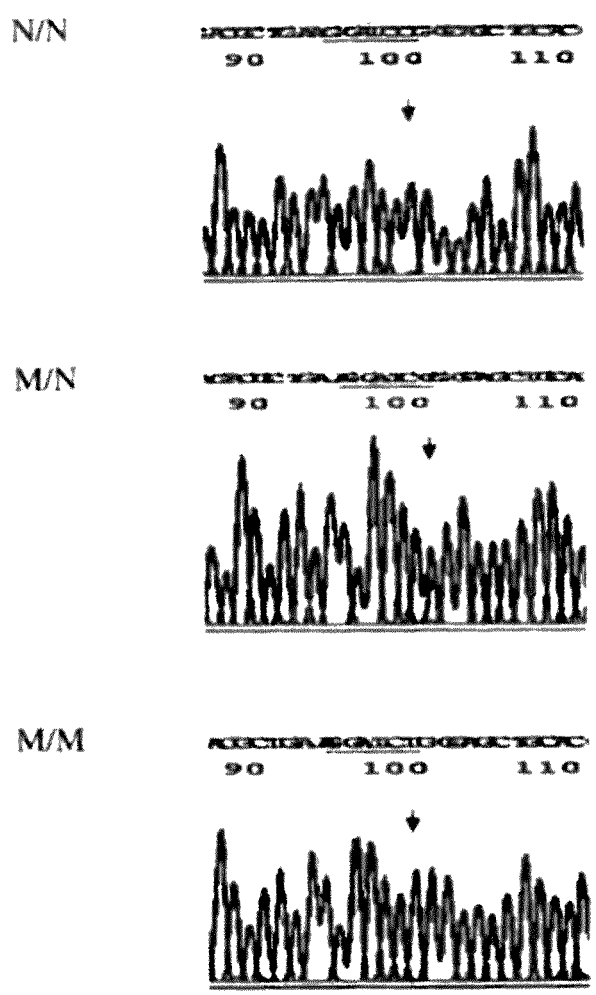

Morgan R., et al. (1998) *Genomic Locations of ANX11 and ANX13 and the Evolutionary Genetics of Human Annexins*, Genomics 48: 100-110.
Rand, J. and Wu, X., (1999) *Antibody-Mediated Disruption of the Annexin-V Antithrombotic Shield: A New Mechanism for Thrombosis in the Antiphospholipid Syndrome*, Thrombosis and Haemostasis 82: 649-655.
Rand, J., et al. (2003) *Human Monoclonal Antiphospholipid Antibodies Disrupt the Annexin A5 Anticoagulant Crystal Shield on Phospholipid Bilayer*, American Journal of Pathology 163: 1193-1200.
Rand, J., et al. (1994) *Reduction of annexin-V (placental anticoagulant protein-I) on placental villi of women with antiphospholipid antibodies and recurrent spontaneous abortion*, American Journal of Obstetrics, Gynecology and Reproductive Science 171: 1566-1572.
Rey, E., et al. (2003) *Thrombophilic disorders and fetal loss: a meta-analysis*, The Lancet 361: 901-908.
Seligsohn U. and Lubetsky A. (2001) *Genetic Susceptibility to Venous Thrombosis*, N. Engl J Med 344: 1222-1231.
Van Heerde W., et al., (2003) *The -1C>T mutation in the annexin A5 gene does not effect plasma levels of annexin A5*, Blood 101: 4223-4224.

\* cited by examiner

Fig. 2

```
  1 CCGAGCCCTG GACAGCTCCC CAGGCCCTTC CCGCGGCGCG AGGACAAGAG

-202
 51 GTC TCCGGGG CCCTCGGGGG AGCGGCGCCT CCTCCTGGTT CCAGCAGCTC

101 TGCGGCCGCT CCCCACCCAG GCCGGCGAGA CCAGCGGGAC AGTCCGCGCC
    NotI

151 GCGGGAGACC AACTGGGACG AGCGGCGACC CACGCAGGCG CGCTGAGGCC

MTF-1     MTF-1              A MTF-1
201 GGGGCAGGGG Cgggacccgc tggcgcgGCC GGCCTGCGGT TGggccccts tsp1
             C  HNF-3    Sp1      Sp1  C   tsp2
251 gcgGGGGTGG GAcggaccaA tCCgggcaGG GCcggggtgg gGCCGCTGgc Myb          tsp3     AP-4, MED-1 A
301 gttTCCGTTG CTTGGATCAG TCTAGGTgca gctgccGGAT CCATTCAGCCT
                                           BamHI +79

351 CTGCATGTCG GCGTCGCCCC GCGTACCGTC GCCCGGCTCT CCGCCGCTCT

401 CCCGGGGGTT CGGGGCACTT GGGTCCCACA GTCTGGGTGA GTGGTCGCAG

451 CCCGGGGAGG GGGCTCCTTC TGGAGAGGAG AGCGTGGTCG CGGGGC
```

GENETIC VARIANT OF THE ANNEXIN A5 GENE

The present non-provisional Application is a divisional of U.S. patent application Ser. No. 11/719,732, filed on Aug. 16, 2007, entitled GENETIC VARIANT OF THE ANNEXIN A5 GENE, which claims the benefit of PCT/EP2005/012259, filed on Nov. 15, 2005, and entitled GENETIC VARIANT OF THE ANNEXIN A5 GENE, which claims the benefit of EP Application No. 04027526.5, filed on Nov. 19, 2004, and entitled GENETIC VARIANT OF THE ANNEXIN A5 GENE, which applications are fully incorporated herein by reference. Also, the entire contents of the ASCII text file entitled "IPM0005US2_Seq_List_ST25.txt" created on Jan. 13, 2012, having a size of 8 kilobytes is incorporated herein by reference.

The present invention relates to a nucleic acid molecule comprising an annexin A5 (ANXA5) gene regulation element which comprises at least one point mutation, whereby said at least one point mutation (substitution) is selected from the group consisting of (i) $_a$ point mutation G to A at a position which corresponds to nucleotide 186 of SEQ ID NO: 2; (ii) a point mutation A to C at a position which corresponds to nucleotide 203 of SEQ ID NO: 2; (iii) a point mutation T to C at a position which corresponds to nucleotide 229 of SEQ ID NO: 2; and (iv) a point mutation G to A at a position which corresponds to nucleotide 276 of SEQ ID NO: 2. Furthermore, the present invention provides for a vector comprising the nucleic acid molecule the invention and a host transformed with the vector. The invention also relates to specific uses, in particular diagnostic uses of the nucleic acid molecules described herein. Moreover, the invention relates to a method for haplotyping an ANXA5 gene regulation element in an individual comprising the steps of: (a) isolating a nucleic acid from a sample that has been removed from the individual; (b) determining the presence of the nucleotides present at positions 186, 203, 229 and 276 of the individual's copy of the ANXA5 gene regulation element, wherein the position numbers are determined by comparison to SEQ ID NO: 2; (c) assigning the individuals a particular haplotype by comparison of the nucleotides present at said positions to the nucleotides recited in the haplotypes as defined herein.

Pregnancy loss is a frequent phenomenon with heterogeneous origin. The most prevalent genetic condition, especially for early pregnancy wastage cases, are chromosomal aberrations. Hypercoagulable disorders that promote thrombosis, collectively termed thrombophilia are yet another significant genetic factor. The most significant defects (3 to 6 fold greater risk for pregnancy loss) include the factor V Leiden mutation, methylenetetrahydrofolatreductase (MTHFR) genetic variants, and factor II (prothrombin) 20210G→A mutation. Among these, the associations of factor V Leiden and prothrombin 20210G→A (PTm) with recurrent pregnancy loss are proven by statistical meta-analysis [Rey, 2003]. The association between some of the MTHFR genetic variants and thrombosis is controversial [Rey, 2003, Key, 2002, Seligsohn, 2001]. Another major factor for repeated pregnancy wastage is the presence of circulating maternal antiphosholipid antibodies (aPL). Increased risks for pregnancy loss have been documented in low-risk and high-risk (more than 3 fetal losses) pregnancies, when aPL are present [Empson, 2002 and references therein].

Annexin A5 (placental anticoagulant protein) is found on normal placental villi and it appears to be reduced in the presence of aPL [Rand, 1994]. Other studies confirm reduced annexin A5 expression on placental trophoblasts of patients with preeclampsia immunohistochemicaly. Annexin A5 is a typical member of the chordate annexin gene family. It projects the essential tetrad structure and calcium-dependent phospholipid binding, which have turned it a key model to study annexin function [Gerke and Moss, 2002]. It is an abundantly and ubiquitously expressed protein mostly present in kidney, liver and placenta [Morgan, 1998]. Annexin A5 could function extracellularly as an inhibitor of blood coagulation and it is proposed that this protein could form a protective anticoagulatory shield on the surface of placental trophoblasts [Rand and Wu, 1999; Rand, 2003].

The annexin A5 gene has been characterized a decade ago [Cookson, 1994] and the gene and encoded protein are extensively studied and characterized. Until recent, little was known however about the regulation of annexin A5 expression. Human annexin A5 (ANXA5) gene produces several transcripts and has a complex promotor with intricate regulation [Carcedo, 2001].

No mutations of annexin A5 have been associated with a disease phenotype, with the exception of the "−1C→T" genetic variant, which is proposed to be protective against myocardial infarction in young patients [Gonzalez-Conejero, 2002]. There are however other data and considerations, disproving the validity of this finding [Kozak, 2003; van Heerde, 2003].

The technical problem of the present invention is the provision of means and methods for determining the risk of pregnancy loss. The solution to this technical problem is provided in the present invention as characterized in the claims and as illustrated and exemplified herein.

The present invention relates to a nucleic acid molecule comprising an annexin A5 (ANXA5) gene regulation element which comprises at least one point mutation, whereby said at least one point mutation (substitution) is selected from the group consisting of (i) a point mutation G to A at a position which corresponds to nucleotide 186 of SEQ ID NO: 2; (ii) a point mutation A to C at a position which corresponds to nucleotide 203 of SEQ ID NO: 2; (iii) a point mutation T to C at a position which corresponds to nucleotide 229 of SEQ ID NO: 2; and (iv) a point mutation G to A at a position which corresponds to nucleotide 276 of SEQ ID NO: 2.

As documented in the appended examples a genetic variant in the promoter region of ANXA5 (BamHI) was surprisingly found in the annexin A5 (ANXA5) gene among women who were examined for different hereditary thrombosis genetic defects because of repeated pregnancy loss. This variant consists of four nucleotide substitutions, which are inherited as a haplotype. Without being bound by theory, these four changes are important for the activity of the annexin A5 promotor and result in a reduced gene expression. As defined herein below, of particular relevance in this respect are four point mutations characterized as "−19 G to A", "1 A to C", "27 T to C" and "76 G to A", whereby "G" denotes guanine, "C" denotes cytosine, "A" denotes adenine and "T" thymine.

The positions "−19", "1", "27" and "76" of the mutations/substitutions described herein relate to the numbering of the sequence as given in appended FIG. 2, depicting the ANXA5 core promoter structure. The numbering in particular relates to the first transcription start point of the gene (tsp 1, as indicated "+1"). However, the corresponding substitutions/mutations are also defined in relation to specific sequences representing the ANXA5 promoter, and given in particular in SEQ ID NO: 2 (an ANXA5 promoter structure as disclosed in Carcedo (2001), Biochem. J. 356, 571-579), SEQ ID NO: 1 (an ANXA5 promoter structure as deposited under gene accession number U0181; NCBI) and as annotated as "human annexin V gene, 5'-untranslated region, exons 1 and 2"; and two further annexin V-promoter regions/ 5'-untranslated regions defined herein as SEQ ID NOS: 3 and 4. The 5'-untranslated region of an annexin V gene may, in context of this invention, in particular be characterized as comprising two specific motifs "A" and "B" which are documented in FIG. 2. A further ANXA V promoter, in accordance with this invention, is a promoter structure which comprises at least one sequence structure as defined in any one of SEQ ID NOs: 17, 18, 19 and 20.

Accordingly, the four substitutions as defined herein relate to the following positions in the corresponding promoter structures as given in SEQ ID NOs: 1 to 4:

| Substitution | SEQ ID NO: 2 | SEQ ID NO: 1 | SEQ ID NO: 3 | SEQ ID NO: 4 |
| --- | --- | --- | --- | --- |
| −19 G → A | 186 | 1259 | 243 | 190 |
| 1 A → C | 203 | 1276 | 262 | 209 |
| 27 T → C | 229 | 1302 | 288 | 235 |
| 76 G → A | 276 | 1349 | 337 | 284 |

These variant nucleotides are represented in repeated pregnancy loss cases at much higher carrier rate as compared to normal female controls with no reported pregnancy problems (nearly two- to three-fold higher). Thus, the BamHI⁻ haplotype represents a risk factor for recurrent pregnancy wastage. Furthermore, these variant nucleotides are represented in repeated pregnancy loss cases at about two-fold higher carrier rate as compared to the normal population of North-West Germany (1.916 fold). The present invention provides for an analytical procedure/method which discriminates this risk haplotype from the normal, wild type allele. In short, the present invention provides for genetic variants of the ANXA5 gene promoter, denoted as "M1" and "M2" (BamHI⁻) alleles. The corresponding "M1 haplotype" comprises the mutations "1 A to C" and "27 T to C", whereas the corresponding "M2 haplotype" comprise all four mutations defined herein above, i.e. in addition the "−19 G to A" mutation and the "76 G to A" mutation. The frequency of these alleles in patients and control groups were estimated. Furthermore, the functional relevance of the ANXA5 M1 and M2 (BamHI⁻) alleles for gene expression of ANXA5 is documented. Most importantly, a relation between carriership of the ANXA5 BamHI⁻ allele and the condition of repeated pregnancy loss is demonstrated and an analytical procedure for distinction of the ANXA5 BamHI⁻ allele from the wild type sequence is established.

In an embodiment of the invention, the nucleic acid molecule comprising an ANXA5 gene regulation element of the invention is a nucleic acid molecule, whereby said at least one point mutation G to A at position 186 of SEQ ID NO: 2 corresponds to (i) a point mutation G to A at a position which corresponds to nucleotide 1259 of SEQ ID NO: 1; (ii) a point mutation G to A at a position which corresponds to nucleotide 243 of SEQ ID NO: 3; or (iii) a point mutation G to A at a position which corresponds to nucleotide 190 of SEQ ID NO: 4.

Furthermore, a nucleic acid molecule is provided which comprises an ANXA5 gene regulation element as defined above, whereby said at least one point mutation A to C at position 203 of SEQ ID NO: 2 corresponds to (i) a point mutation A to C at a position which corresponds to nucleotide 1276 of SEQ ID NO: 1; (ii) a point mutation A to C at a position which corresponds to nucleotide 262 of SEQ ID NO: 3; or (iii) a point mutation A to C at a position which corresponds to nucleotide 209 of SEQ ID NO: 4; and/or whereby said at least one point mutation T to C at position 229 of SEQ ID NO: 2 corresponds to (i) a point mutation T to C at a position which corresponds to nucleotide 1302 of SEQ ID NO: 1; (ii) a point mutation T to C at a position which corresponds to nucleotide 288 of SEQ ID NO: 3; or (iii) a point mutation T to C at a position which corresponds to nucleotide 235 of SEQ ID NO: 4; and/or whereby said at least one point mutation G to A at position 276 of SEQ ID NO: 2 corresponds to (i) a point mutation G to A at a position which corresponds to nucleotide 1349 of SEQ ID NO: 1; (ii) a point mutation G to A at a position which corresponds to nucleotide 337 of SEQ ID NO: 3; or (iii) a point mutation G to A at a position which corresponds to nucleotide 284 of SEQ ID NO: 4.

In a preferred embodiment of the invention, the nucleic acid molecule comprising an ANXA5 gene regulation element comprising at least one point mutation as defined herein comprises at least one of the following sequences (i) TGCGGTTGGGGC (SEQ ID NO: 17); (ii) TGGCGGGGGTGGGACGGGCCAAGCCGGGCA-GGGCCGGGGTGGGGC (SEQ ID NO: 18), (iii) GCTG-GCGTTTCCGTTGCTTGGATCAGTCTAGGTG CAGCTGC (SEQ ID NO:19); or (iv) GGATCC (SEQ ID NO: 20), whereby the G in SEQ ID NO: 17 may be an A (corresponding to −19 G to A), whereby said A in SEQ ID NO: 18 may be a C (corresponding to 1 A to C), whereby said T in SEQ ID NO: 18 may be a C (corresponding to 27 T to C) and whereby said G in SEQ ID NO: 20 may be an A (corresponding to 76 G to A).

As documented herein above, in a most preferred embodiment of the present invention, the nucleic acid molecule defined herein as an ANXA5 gene regulation element is a promoter. Accordingly, most preferably, the nucleic acid molecule is capable of conferring the activity of the annexin A5, in particular in form of annexin A5/V expression. Said expression may be tested by methods known in the art, for example by operatively linking the nucleic acid molecule of the present invention to either a marker molecule to be expressed and/or to the coding sequence of annexin A5 and detecting whether said annexin A5 or said marker molecule is expressed in, inter alia, an heterologous gene expression system.

Also comprised in the definition of an ANXA5 promoter/ regulatory sequence of the present invention are nucleic acid molecules which are at least 60%, more preferably at least 70%, more preferably at least 80%, more preferably at least 90% and most preferably at least 95% identical to the promoter sequences as shown in any one of SEQ ID NOs: 1 to 4.

The ANXA5 promoter as defined herein is accordingly, a promoter that is highly homologous to the promoter sequences as defined in any one of SEQ ID NOs: 1 to 4 or in appended FIG. 2 and which is capable of driving an ANXA5 expression in cells, whereby, these cells are selected from the group consisting of: HeLa, HEK293, HepG3 BeWo, placental trophoblasts, hepatocytes and epithelial cells of kidneys. Another aspect of the invention relates to the above defined regulatory sequences or uses of regulatory sequences (comprising the herein defined substitution) which hybridize to one of the above-described regulatory sequences of the invention, preferably to the complementary, strand thereof, and comprise at least one of the substitutions provided in this invention. Preferably, said hybridizing sequence comprises, in its complementary strand, at least two substitutions as provided herein.

These hybridizing sequences may be promoters as defined above or regulatory elements comprising, in their complementary strand, (a) substitution(s) as defined herein. The term "hybridize" as used refers to conventional hybridization conditions, preferably to hybridization conditions at which 5xSSPE, 1% SDS, 1x Denhardt's solution is used as a solution and/or hybridization temperatures are between 35° C. and 70° C., preferably 65° C. After hybridization, washing is preferably carried out first with 2x SSC, 1% SDS and subsequently with 0.2x SSC at temperatures between 35° C. and 70° C., preferably at 65° C. (regarding the definition of SSPE, SSC and Denhardt's solution see Sambrook, loc. cit.). Stringent hybridization conditions as for instance described in Sambrook, supra, are particularly preferred. Particularly preferred stringent hybridization conditions are for instance present if hybridization and washing occur at 65° C. as indicated above. Non-stringent hybridization conditions, for instance with hybridization and washing carried out at 45° C. are less preferred and at 35° C. even less.

In a particular preferred embodiment the nucleic acid molecule of the invention which is operatively linked to a gene encoding for a marker protein, a signal protein or a reporter gene.

The invention relates in one embodiment said marker or receptor gene to be expressed under the control of the herein disclosed regulatory sequences are, e.g., fluorescent proteins (e.g. green fluorescent protein) or proteins which may, directly or indirectly, lead to a visible or measurable signal, when expressed (e.g., chloramphenicol acetyl transferase, beta-galactosidase).

Examples of marker or reporter genes, which allow the expression activity of regulatory sequences, preferably promoters, to be detected, preferably in eukaryotic cells, are described in the literature. Examples of reporter genes encode luciferase, (green/red) fluorescent protein and variants thereof, like eGFP (enhanced green fluorescent protein), RFP (red fluorescent protein, like DsRed or DsRed2), CFP (cyan fluorescent protein), BFP (blue fluorescent protein), YFP (yellow fluorescent protein), β-galactosidase or chloramphenicol acetyltransferase, and the like.

For example, GFP can be from *Aequorea victoria* (U.S. Pat. No. 5,491,084). A plasmid encoding the GFP of *Aequorea victoria* is available from the ATCC Accession No. 87451. Other mutated forms of this GFP including, but not limited to, pRSGFP, EGFP, RFP/DsRed, and EYFP, BFP, YFP, among others, are commercially available from, inter alia, Clontech Laboratories, Inc. (Palo Alto, Calif.). For example, DsRed2 is also available from Clontech Laboratories, Inc. (Palo Alto, Calif.); see appended examples. Also further luminescent proteins may be expressed under the control of the regulatory sequence provided herein. In this context, a nucleotide sequence coding, inter alia, for a protein of the luciferase family is envisaged.

The invention also relates to a recombinant nucleic acid molecule comprising the regulatory sequence of the invention and a gene under its control, whereby said gene encodes a tag. Said tag may be selected from the group consisting of a His-Tag, glutathione, a Strep-tag, a Flag-tag, CBP (Calmodulin-binding peptide), TAG-100 (available from Quiagen), E2-tag (from bovine papillomavirus type I transactivator protein E2) and Z-tag, but is not limited thereto. For example, the self-cleavable chitin-binding tag (e.g. from IMPACT-CN System) or influenza hemagglutinin (HA) may be employed in accordance with this invention.

Accordingly, the invention also relates to an isolated nucleic acid molecule comprising the nucleic acid molecule representing an ANXA5 promoter as defined herein and comprising at least one substitution as defined herein, whereby said inventive nucleic acid molecule is operatively linked to a nucleic acid molecule sequence which is capable of conferring the activity of a reporter gene. Also provided is, accordingly, a recombinant nucleic acid molecule of the invention.

Accordingly, the invention also provides specific recombinant nucleic acid molecules comprising the regulatory sequence described herein. Said recombinant nucleic acid molecule comprises the regulatory sequences in an "isolated" form, preferably in combination with a heterologous nucleic acid sequence to be expressed. As used herein, the term "isolated" when used in conjunction with a nucleic acid molecule/regulatory sequences of the present invention refers to a nucleic acid molecule which has been separated from an organism in a substantially purified form (i.e. substantially free of other substances originating from that organism), or a nucleic acid molecule having the same nucleotide sequence but not necessarily separated from the organism (i.e. synthesized or recombinantly produced nucleic acid molecules). Preferably and most envisaged, the regulatory sequences described in the present invention are operatively linked to additional, heterologous nucleic acid sequences in a recombinant nucleic acid molecule. As detailed herein below, said additional nucleic acid sequence may be a coding gene as well as a nucleic acid sequence which, upon expression, leads to the production of other nucleic acid molecules, like an antisense construct, a ribozyme or the like.

As employed herein, the term "heterologous nucleic acid molecule", means a nucleic acid molecule which is preferably operatively linked to the regulatory sequence described above but is not a nucleic acid molecule which codes for annexin 5 or a fragment thereof. Therefore, said "heterologous nucleic acid molecule" originates from a different genetic context than the regulatory sequence described above. Non-limiting examples of such "heterologous nucleic acid molecules" are given herein below and comprise in particular marker molecules, like luciferase, galactosidase, fluorescent proteins, GFP, eGFP, DsRed, etc. or tag-molecules, like Flag-tags, CBP and others. Yet, also other receptor genes, surface proteins are envisaged. Also nucleic acid molecules which do not encode proteins are envisaged as "heterologous nucleic acid molecules". Such nucleic acids comprise, but are not limited to, anti-sense molecules, aptamers, ribozymes, inhibiting RNA molecules and the like, being particularly useful in a research setting.

The term "recombinant nucleic acid molecule" relates to nucleic acid molecules originating from a different genetic context and combined by molecular biological methods. Here, the term "different genetic context" relates to genomes from different species, varieties or individuals or different positions within a genome. Recombinant nucleic acid molecules can contain not only natural sequences but also sequences, which, compared to the natural ones are mutated or chemically modified or else, the sequences are altogether newly synthesized sequences.

The recombinant nucleic acid molecules of the invention show one or more of the above-described regulatory sequences in combination with sequences from another genetic context. An example of a recombinant nucleic acid molecule contains one or more regulatory sequences of the invention or a minimal promoter derived and obtainable from the sequences disclosed herein in combination with a gene other than the annexin AS gene, preferably other than the human annexin A5 gene. The term "recombinant nucleic acid molecule", therefore, does not relate to a nucleic acid molecule which comprises an annexin A5 coding sequence under the control of the regulatory sequences provided herein.

Moreover, the recombinant nucleic acid molecules can contain, apart from a promoter containing one or more regulatory sequences of the invention, a polylinker sequence located downstream thereof and comprising one or more restriction sites into which nucleotide sequences can be cloned by methods known to a skilled person, which thus come under the expression control of the promoter.

Furthermore, the recombinant nucleic acid molecule described herein may contain a transcription termination signal downstream of the polylinker. Examples of suitable termination signals are described in the state of the art. The termination signal can, for instance, be the thymidine kinase polyadenylation signal. The herein-described recombinant nucleic acid molecules which preferably contain a nucleotide sequence to be expressed can be directly employed for uses within the meaning of the invention, such as DNA transfections, the generation of genetically modified host cells or non-human transgenic animals. Furthermore, said recombinant molecules can be employed in screening methods described herein as well as in medical and scientific settings. As defined above, the nucleic acid molecule of the invention may be DNA, RNA as well as PNA. Therefore, in accordance with the present invention, the term "nucleic acid molecule" comprises also any feasible derivative of a nucleic acid to which a nucleic acid probe may hybridize. Said nucleic acid probe itself may be a derivative of a nucleic acid molecule capable of hybridizing to said nucleic acid molecule or said derivative thereof. The term "nucleic acid molecule" further comprises peptide nucleic acids (PNAs) containing DNA analogs with amide backbone linkages (Nielsen, Science 254 (1991), 1497-1500).

Also provided in context of this invention is a vector comprising the nucleic acid molecule as defined herein. Said vector may, inter alia, be an expression vector or a gene transfer vector.

The term "vector" relates to circular or linear nucleic acid molecules which can autonomously replicate in host cells into which they are introduced. The vectors may contain the above-characterized recombinant nucleic acid molecules in their full length or may contain, apart from the regulatory sequences of the invention, the components described for the recombinant nucleic acid molecules, such as minimal promoter (comprising at least one of the substitutes defined herein), polylinker and/or termination signal.

The vectors of the invention may be suitable for replication in prokaryotic and/or eukaryotic host cells. They contain a corresponding origin of replication. The vectors are preferably suitable for replication in mammalian cells, particularly preferably in human cells.

The vectors of the invention preferably contain a selection marker. Examples of selection marker genes are known to a skilled person. Selection marker genes which are suitable for selection in eukaryotic host cells are for instance genes for dihydrofolate reductase, G418 or neomycin resistance.

The vectors of the invention are preferably expression vectors for expression in eukaryotic cells. Such vectors can be constructed starting from known expression vectors by replacement of their promoter or the sequences not belonging to a minimal promoter with the regulatory sequences of the invention or by supplementation with regulatory sequences (regulatory elements) of this invention. Examples of expression vectors which can be modified in this way are pcDV1 (Pharmacia), pRC/CMV, pcDNA1 or pcDNA3 (Invitrogen).

Also provided is a host transformed with the vector as defined herein, whereby said host is, preferably selected from the group consisting of a mammalian cell, an amphibian cell, an insect cell, a fungal cell, a plant cell and a bacterial cell. Non-limiting examples of mammalian cells are HeLa-cells, HepG2 cells, CHO cells, 293-cells and COS-cells as mentioned below. Suitable bacterial cells are those which are generally used for cloning, such as *E. coli* or *Bacillus subtilis*. Examples of fungal cells are yeast cells, preferably those of the genera *Saccharomyces* or *Pichia*, particularly preferably, of *Saccharomyces cerevisiae* or *Pichia pastoris*. Suitable animal cells include for instance insect cells, vertebrate cells, preferably mammalian cells, such as CHO, COS7, HeLa, NIH3T3, MOLT-4, Jurkat, K562, HepG2, 293-cells and the like. Yet, also cultured primary cells are envisaged, like placental trophoblasts or kidney or liver primary cells/cell cultures. Further suitable cell lines are described in the art and can for instance be obtained from the Deutsche Sammlung fur Mikroorganismen and Zellkulturen (DSMZ, Braunschweig). In this context it is of note that the host cells may be transfected with a regulatory sequence, a recombinant nucleic acid sequence or a vector of the invention. These transfected cells are particularly useful in scientific methods for the elucidation of the function of an ANXA-5 promoter and/or expressed ANXA5. Yet, these cells may be employed in screening systems, for example high-throughput screenings, where compounds are tested for their capacity to activate or silencing the regulatory sequence of the invention, comprising at least one mutation as defined herein.

Also envisaged in the present invention is a non-human transgenic organism, which are hosts in the sense of the present invention and which comprise a nucleic acid molecule as defined herein, i.e. an annexin 5 promoter comprising at least one mutation as provided in this invention. In a further preferred embodiment, the invention relates to a genetically modified cell/host cell which comprises the ANXA5 regulatory sequence comprising at least one mutation as defined herein, the recombinant nucleic acid molecule or the vector as described above. Also provided is/are (a) method(s) for preparing genetically modified host cells, characterized in that the host cells are transfected with one of the above-described vectors and the transfected host cell is cultured in a culture medium.

The term "genetically modified" means that the host cell or the host contains, in addition to the natural genome, a nucleic acid molecule or a vector of the present invention, which has been introduced into the host cell or the host or into a precursor. The nucleic acid molecule or the vector can be present in the genetically modified host cell/host either as an independent molecule outside the genome, preferably as a replicable molecule, or may be stably integrated in the genome of the host cell or host. The introduction of a vector into host cells can be carried out according to known standard methods as for instance described in Sambrook (Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.)). Examples of applicable transfection techniques are calcium phosphate transfection, DEAE dextran-mediated transfection, electroporation, transduction, infection, lipofection or biolistic transfer.

The invention relates in a preferred embodiment to an isolated nucleic acid molecule selected from the group consisting of haplotype M1 and M2, wherein haplotype M1 comprises a sequence as shown in SEQ ID NO: 2 and whereby said sequence has on position 203 a substitution from A to C and on position 229 a substitution from T to C and wherein haplotype M2 comprises a sequence as shown in SEQ ID NO: 2 and whereby said sequence has an position 186 a substitution from G to A, on position 203 a substitution from A to C, on position 229 a substitution from T to C and on position 276 a substitution from G to A. The definition of the "M1" as well as the "M2" haplotype are also given in the appended examples. The "M1" and "M2" haplotype also relate to the specific point mutations provided herein and characterized in any of the further ANXA5 promoter structures provided in any of SEQ ID NOS: 1, 3 or 4 or as shown in appended FIG. 2. Accordingly, the invention also provides for an isolated nucleic acid molecule selected from the group consisting of haplotype M1 and M2, wherein said haplotype M1 comprises a point mutation as defined as 1 A→C and a point mutation as defined as 27 T→C, and wherein said haplotype M2 comprises all four point mutations as defined herein, i.e. the addition mutations −19 G→A and 76 G→A.

Also provided is a method for haplotyping an ANXA5 gene regulation element in an individual comprising the steps of (a) isolating a nucleic acid from a sample that has been removed from the individual; (b) determining the presence of the nucleotides present at positions 186, 203, 229 and 276 of the individual's copy of the ANXA5 gene regulation element, wherein the position numbers are determined by comparison to SEQ ID NO: 2; (c) assigning the individuals a particular haplotype by comparison of the nucleotides present at said positions to the nucleotides recited in the haplotypes as defined as "M1" or "M2" herein above.

In a medical setting, in vitro methods for diagnosing are particularly important. The present invention provides for important tools, with which specific "genetic variants" of the ANXA5 promoter region may be detected and whereby said detection is indicative for a higher risk of pregnancy loss/ wastage and/or a higher risk of the development of anti- phospholipid antibodies. The presence of antiphospholipid antibodies in the circulation of the mother is associated with increased fetal loss risk of both, low-risk and high-risk pregnancies, as documented in, inter alia, Empson (2002).

Without being bound by theory, the present invention reasons that the documented reduced expression of ANX A5 gene, due to the herein documented allelic variation in its promoter sequence, could be a direct cause for lower annexin A5 enrichment on the plancentar surface and is very likely to cause development of antiphospholipid antibodies.

Therefore, the invention also provides for an in vitro method for diagnosing or detecting a predisposition for a tendency to pregnancy loss (waste) and/or the development of antiphospholipid antibodies, said method comprising the steps of (a) examining an ANXA5 gene regulation element to detect at least one point mutation/substitution as defined in this invention; and (b) determining whether any, of the at least one of said point mutations is present. Said in vitro method may be carried out by methods known in the art, as described herein below and as documented in the appended examples.

As shown in the examples, the invention provides for an in vitro method for diagnosing or detecting a predisposition or a tendency to pregnancy loss (waste), said method comprising the steps of (a) haplotyping an individual in accordance with the methods provided herein; (b) determining whether said individual has an haplotype "M1" or "M2" as defined herein or a "normal"/"wildtype" haplotype "N", whereby the haplotype N does not comprise a point mutation/substitution as defined in the invention; (c) determining whether said individual has a genotype N/N, M1/N, M2/N, M1/M1, M2/M2 or M1/M2. The corresponding method is also useful in diagnosing or detecting a predisposition to or a tendency to develop anti-phospholipid antibodies.

As shown in the examples, a "heterogenous" or "homogenous" individual, i.e. an individual bearing a "genotype" M2/N, M2/M2 or M1/M2 has a particular higher risk of pregnancy loss and should be provided with closer medical care and supervision during pregnancy. The person skilled in the art may also determine the further haplotypes, like M1/N or M1/M1 in order to take specific measures in medical care and supervision, even if the "M1-haplotype" is associated with a lower or even normal risk of pregnancy loss in comparison to the "M2 haplotype". As pointed out above, the detection of at least one point mutation as described herein or of a haplotype as described herein can be carried out by standard methods known in the art. For example, the detection of said at least one point mutation in said ANXA5 gene regulation element or said haplotyping may be carried out or determined by nucleic acid techniques based on size or sequence. Said technique based on size or sequence may be selected from the group consisting of hybridization techniques, nucleic acid sequencing, PCR, restriction fragment determination, single nucleotide polymorphism (SNPs)-determination, LCR (ligation chain reaction) or restriction fragment length polymorphism (RFLP)-determination. Corresponding examples and further details may be obtained from standard technical advise literature (like Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.)). As documented in the appended examples, a particular preferred method in context of this invention is the restriction fragment determination or the RFLP method, particularly preferred comprising the determination of a BamHI restriction site. As shown herein, the absence (BamHI⁻) or the presence (BamHI⁺) of a BamHI restriction site is determined, and is indicative for the absence or presence of a point mutation as defined herein. Details on this method are given in the appended examples and herein below. In one embodiment, a relevant DNA-stretch may be amplified from genomic DNA by PCR-technology. Potential primers to be employed comprise, but are not limited to, the primers as provided in SEQ ID NO: 22 (ANX5.P.F) and SEQ ID NO: 23 (ANX5.exI.R). The person skilled in the art is readily in the position to deduce further primer pairs or primers to be employed in order to amplify relevant stretches of the herein defined annexin A5 (ANXA5) regulation element/promoter. After the amplicon is obtained (see also experimental part) it can be digested (restriction digest) with the restriction enzyme BamHI (which can be obtained from various suppliers, inter alia: Roche Applied Science, Mannheim, Germany; MBI Fermentas, St. Leon-Rot, Germany; New England Biolabs, Frankfurt am Main, Germany. Again, details are given in the experimental part. After this digest, to be carried in accordance with methods well-known in the art (see inter alia Sambrook/Russel, 2001, (log.cit.)), further analysis of the BamHI⁻/BamHI⁺ restriction site can be carried out by known techniques, like gel analysis, e.g. agarose gel analysis (see also experimental part and, illustratively, appended FIG. 4). In a preferred embodiment of the uses and methods of the invention said BamHI restriction site is the restriction side corresponding to nucleotides 276 to nucleotides 281 of SEQ ID NO: 2; to nucleotide 1349 to nucleotides 1354 of SEQ ID NO: 1; to nucleotide 337 to nucleotides 342 of SEQ ID NO: 3 or corresponds to nucleotides 284 to 289 of SEQ ID NO: 4.

The absence of said BamHI restriction site (BamHI⁻) is indicative for a predisposition for pregnancy loss, as already shown in the appended examples.

The in vitro methods of the invention may also comprise the detection of said at least one point mutation described herein or said haplotyping as described herein, whereby suitable PCR (polymerase chain reaction) primers are used. For example, (a) a point mutation corresponding to the substitution defined as −19 G→A herein may comprise the use of a forward primer as defined in SEQ ID NO: 8 or 9 and a reverse primer as defined in SEQ ID NO: 10 (or SEQ ID NO: 13); (b) a point mutation corresponding to the substitution defined as 1 A→C herein may comprise the use of a forward primer as defined in SEQ ID NO: 11 or 12 and a reverse primer as defined in SEQ ID NO: 13 (or SEQ ID NO: 10); (c) a point mutation corresponding to the substitution defined as 27 T→C herein may comprise the use of a forward primer as defined in SEQ ID NO: 14 or 15 and a reverse primer as defined in SEQ ID NO: 16 (or SEQ ID NO: 7); and (d) a point mutation corresponding to the substitution defined as 76 G→A herein may comprise the use of a forward primer as defined in SEQ ID NO: 5 or 6 and a reverse primer as defined in SEQ ID NO: 7 (or SEQ ID NO: 16).

Also the haplotyping as described above may be carried out by employing primers (e.g. in PCR reactions and the like. Preferably, said haplotyping comprises the use of primers as shown in SEQ ID NOS: 5 to 16.

In a most preferred embodiment of the invention, the absence or presence of a point mutation/substitution corresponding to position 276 of an ANXA5 gene regulation element as shown in SEQ ID NO: 2 is determined, said point mutation/substitution being preferably a G to A substitution.

As shown in the appended examples, the in vitro methods provided herein are most preferably carried out on genomic DNA and said genomic DNA is isolated from a biological sample.

Biological sample may be, without being limited, selected from the group consisting of blood, serum, urine, amniotic fluid, vaginal secretions, nipple aspirates, sputum and mucous epithelial samples.

The present invention is particularly useful in the monitoring of pregnant women or the monitoring of women who intend to get pregnant. Since the methods of the present invention may be carried out on genomic DNA from said women, corresponding samples may be easily obtained, e.g. with buccal swabs.

The invention also provides for a kit comprising at least one primer pair as defined herein above. Said kit is particularly useful in the preparation of a diagnostic composition for diagnosing or detecting a predisposition for or a tendency to pregnancy loss, and/or for diagnosing or detecting a predispositions for a tendency to develop anti-phospholipid antibodies.

Accordingly, the invention also relates to the use of at least one primer pair as defined herein the preparation of a diagnostic composition for diagnosing or detecting a predisposition for or a tendency to pregnancy loss and/or for diagnosing or detecting a predisposition for the development of anti-phospholipid antibodies.

Further provided is the use of a nucleic acid molecule comprising at least one point mutation as defined herein the preparation of a diagnostic composition for diagnosing or detecting a predisposition for or a tendency to pregnancy loss and/or for diagnosing or detecting a predisposition or a tendency for the development of anti-phospholipid antibodies. Said nucleic acid molecule is particularly useful in diagnostic methods as comparative marker and/or standard comprising at least one defined mutation as described herein.

Disclosed in the present invention are means and methods for screening, in particular, genomic DNA for the presence or absence of specific point mutations in the ANXA5 gene regulation element. Therefore, also provided is a method of diagnosing or detecting a predisposition for or a tendency to pregnancy loss in an individual and/or a method of diagnosing or detecting a predisposition or a tendency for the development of anti-phospholipid antibodies comprising the step of determining whether said individual carries at least one of the at least one point mutations/substitutions as defined herein, namely, the −19 G→A, the 1 A→C, the 27 T→C and/or the 76 G→A substitution.

Said method of diagnosing or detecting may comprise the in vitro methods for detecting a point mutation as disclosed herein above. The method of diagnosing is most preferably employed in screening of women who are pregnant or who intend to become pregnant. Corresponding methods and analysis of the results obtained are provided in the appended, non-limiting examples.

In a further embodiment of the present invention is provided a method of screening for molecules which are capable of interacting with a mutated ANXA5 gene regulation element as defined herein above, comprising the steps of (a) contacting a nucleic acid molecule of comprising at least one mutation in the ANXA5 gene regulatory element as provided herein or contacts a vector or a host comprising such a nucleic acid molecule with a candidate molecule; (b) measuring and/or detecting a response; and (c) comparing said response to a standard response as measured in the absence of said candidate molecule.

In the provided screening method for interacting molecules the above defined, nucleic acid molecules comprising a gene regulatory element as defined herein (and comprising at least one mutation as disclosed in their invention) and being operatively linked to a reporter and/or marker gene are particularly useful. The compounds to be screened are screened for their direct or indirect interaction of the regulatory sequence provided herein.

Said "contacting" may be carried out in vivo as well as in vitro. It is, e.g.

envisaged that said transgenic animal is contacted in vivo with the compound/candidates to be tested. Said compound(s) may, inter alia, be injected to said animal, for example by inter-cerebral/inter-cranial injection. Similarly, cells transfected with a recombinant nucleic acid molecule as disclosed herein may be contacted in vitro with the compounds to be tested, for example by introducing the test compounds into the culture medium. The detection, whether said compound(s) is/are capable of interacting with regulatory sequence of the invention, may involve the detection, whether the regulatory sequence is activated. A good cell system to be used in order to assess whether the mutated ANXA5 gene regulatory sequence is active may be selected from the group consisting of HeLa, HEK293, HepG2, BeWo cells, kidney cells and the like. The response obtained when screening a compound interacting with the mutated ANXA5 gene regulatory sequence may be compared to a response obtained with the same compound to be screened and using a non-mutated, "wild-type" ANXA5 gene regulatory sequence.

The term "contacting a recombinant nucleic acid molecule of the invention with (a) compound(s) suspected to directly or indirectly interact said the regulatory sequence" may comprise tests of interaction. Such tests may be carried out by specific immunological, biochemical assays and/or genetic assays which are known in the art and comprise homogenous and heterogeneous assays. For example, in the method of the present invention, the interaction assays to be employed in accordance with this invention may be used to detect as a response the direct or indirect interaction of the regulatory sequence with the candidate molecule. Said interaction assays employing read-out systems are well known in the art and comprise, inter alia, two hybrid screenings, (as, described, inter alia, in EP-0 963 376, WO 98/25947, WO 00/02911 and modified for detection of interaction partners for the regulatory sequences of the invention), GST-pull-down columns, co-precipitation assays from cell extracts as described, inter alia, in Kasus-Jacobi, Oncogene 19 (2000), 2052-2059, "interaction-trap" systems (as described, inter alia, in U.S. Pat. No. 6,004,746), in vitro binding assays and the like. Further interaction assay methods and corresponding read out systems are, inter alia, described in U.S. Pat. No. 5,525,490, WO 99/51741, WO 00/17221, WO 00/14271, WO 00/05410. Of particular relevance in accordance with this invention are interaction assays which comprise biochemical/genetic methods like, e.g. band shift assays which are employed to deduce, inter alia, proteineous compounds capable of interacting with regulatory sequences/promoters, in particular with promoters comprising at least one mutation as provided herein.

Furthermore, the above recited method for screening of compounds capable of regulating the ANXA5 promoter and in particular an ANXA5 promoter comprising at least one mutation as defined herein may comprise the screening for substances which are capable to induce a differentiation and/or a gene expression program in a test/host cell comprising the regulatory sequence of the present invention. Said screening methods may also comprise the screening of compounds which activate, directly or indirectly, the mutated regulatory sequence of ANXA5 as defined herein. Accordingly, the present invention also provides for drug screening methods, whereby these drugs may be useful in the treatment or prevention of disorders relating to pregnancy loss/wastage and/or the development of anti-phospholipid antibodies.

An agent is, accordingly, capable of "interacting with the regulatory sequence" of the present invention, when a corresponding readout scores positively or negatively. For example, a candidate agent may provoke the expression of a marker or reporter gene, like eGFP, DsRed or GFP under the control the herein described mutated ANXA5-regulatory sequence. In this case, the candidate compound has, either directly or indirectly, interacted with said regulatory sequence. A direct interaction is, inter alia, envisaged from a specific transcription factor capable of binding to the mutated regulatory sequence of the invention and of eliciting the transcription. An example of indirect interaction of the candidate compound comprises, but is not limited to, the involvement of a signal transduction pathway.

The above mentioned comparison between the response upon contacting the mutated regulatory sequence of the invention with said candidate molecule and the standard response as measured in the absence of said candidate molecule as measured in comparison to a non-mutated (wildtype) ANXA5 gene regulatory sequence may provide for the presence, the absence, the decrease or the increase of a specific signal in the readout system. Said readout system, as described herein may be a, e.g., a biochemical or a physiological readout system. Genetic readout systems are also envisaged. A specific signal which is increased over the standard signal/response may thereby be classified as being an activator of the mutated ANXA5 regulatory sequence provided herein, whereas a decreased signal may be classified as being diagnostic for an inhibitor of ANXA5 regulatory sequence function or expression.

Of particular use in the present invention is also a nucleic acid fragment of the nucleic acid molecules as defined above, namely of a mutated ANXA5 regulatory sequence, wherein said fragment comprises at least 15 nucleotides and wherein said fragment comprises at least one point mutation/substitution as defined herein. Said nucleic acid fragment may be particularly useful in screening methods provided herein. Similarly useful are oligomers consisting of at least one sequence and having a length of at least 20 nucleotides, which is capable of specifically hybridizing to a nucleic acid molecule as defined herein, i.e. a ANXA5 mutated regulatory sequence comprising at least one mutation as defined herein. Said oligomer should be capable of hybridizing to nucleic acid fragments comprising at least 15 nucleotides and comprising at least one point mutation as defined herein.

Therefore, the invention also provides for an oligomer consisting essentially of at least one base sequence and having a length of at least 10 nucleotides which hybridizes or is capable of hybridizing to the nucleic acid fragments as defined above and comprising at least one point mutation as provided herein. As specific example of such an oligomer is or comprises the nucleic acid sequence as shown in SEQ ID NO: 21. The oligomers described here may be, inter alia, an oligonucleotide or a peptide nucleic acid (PNA)-oligomer.

Also comprised in this invention is a set of oligomers comprising, at least two oligomers as defined herein. Said oligomers and/or said set of oligomers are particularly useful in the screening methods as well as the diagnostic uses provided herein. Accordingly, the invention also relates to the use of an oligonucleotide/oligomer as defined above or of a set of oligomers provided herein for detecting a point mutation/substitution as defined in this invention, or for detecting single nucleotide polymorphisms (SNPs) within sequences taken from SEQ ID NOS: 1, 2, 3 or 4.

The oligomers provided herein and capable of interacting with nucleic acid molecules comprising at least one point mutation as provided herein may also be useful in high throughput (HTPs)-screenings. Accordingly, these oligomers may also be employed in the production of "gene analysis" or "gene chips". The invention therefore also provides for a method for manufacturing an arrangement of different oligomers (array) fixed to a carrier material, said method comprising the coupling of at least one oligomer or a set of oligomers as defined herein to a solid phase. Also comprised is an arrangement of oligomers (array) obtainable by the method for manufacturing as disclosed above.

The preparation of arrays is well known in the art. An overview of the prior art in oligomer array manufacturing can be gathered from a special edition of Nature Genetics (Nature Genetics Supplement, Volume 21, January 1999), published in January 1999, and from the literature cited therein. Fluorescently labeled probes are often used for the scanning of immobilised DNA arrays. The simple attachment of Cy3 and Cy5 dyes to the 5'-OH of the specific probe are particularly suitable for fluorescence labels. The detection of the fluorescence of the hybridised probes may be carried out, for example via a confocal microscope. Cy3 and Cy5 dyes, besides many others, are commercially available.

According to the present invention, it is preferred that an arrangement of different oligonucleotides and/or PNA-oligomers (a so-called "array") made available by the present invention is present in a manner that it is likewise bound to a solid phase. This array of different oligonucleotide- and/or PNA-oligomer sequences can be characterised in that it is arranged on the solid phase in the form of a rectangular or hexagonal lattice. The solid phase surface is preferably composed of silicon, glass, polystyrene, aluminum, steel, iron, copper, nickel, silver, or gold. However, nitrocellulose as well as plastics such as nylon which can exist in the form of pellets or also as resin matrices are suitable alternatives.

Therefore, a further subject matter of the present invention is a method for manufacturing an array fixed to a carrier material for the improved treatment and monitoring of breast cell proliferative disorders. In said method at least one oligomer according to the present invention is coupled to a solid phase. Methods for manufacturing such arrays are known, for example, from U.S. Pat. No. 5,744,305 by means of solid-phase chemistry and photolabile protecting groups.

A further subject matter of the present invention relates to a DNA chip for the improved treatment and monitoring of pregnant women or women who are to be monitored for a potential pregnancy. The DNA chip contains at least one nucleic acid according to the present invention. DNA chips are known, for example, in U.S. Pat. No. 5,837,832.

Moreover, a subject matter of the present invention is a kit which may be composed, for example, a set of primer oligonucleotides containing at least two oligonucleotides whose sequences in each case correspond to or are complementary to an at least 10, preferably at least 18 base long segment of the base sequences specified in SEQ ID NOs: 1 to 4 which comprise at least one mutation as provided herein. The above recited methods and assays are preferably used in the screening of genomic DNA. Genomic DNA is obtained from DNA of cell, tissue or other test samples using standard methods. This standard methodology is found in references such as Fritsch and Maniatis eds., Molecular Cloning: A Laboratory Manual, 1989.

The present invention provides methods and nucleic acids for the analysis of biological samples for features associated with the development anti-phospholipid antibodies and/or the prognosis of pregnancy loss/wastage. The invention is characterised in that the nucleic acid suspected to comprise at least one mutation as provided herein is/are contacted with a reagent or series of reagents capable of distinguishing between a nucleic acid comprising said mutation(s) and a wildtype ANXA5 promoter sequence within the genomic sequence (or within a part of said genomic sequence) of interest. The present invention makes available a method for ascertaining genetic parameters of genomic DNA. The method is for use for the determining the prognosis of potential pregnancy loss/wastage. The invention presents improvements over the state of the art in that by means of the methods and compounds described herein a person skilled in the art may carry out a sensitive and specific detection assay of cellular matter comprising the specific mutations provided herein. This is particularly useful as it allows the analysis of samples of, e.g., body fluids. The generated information is useful in the selection of a treatment or a monitoring of the patient. If a mutation as provided herein is determined a further treatment might be necessary.

Most of the techniques provided herein are based on known molecular biology methods and comprise the use of specific probes and/or primers which are capable of detecting/amplifying nucleic acid molecules comprising at least one mutation as defined herein.

In a preferred embodiment said methods are achieved by contacting nucleic acid sequences in a biological sample obtained from a subject with at least one reagent or a series of reagents, wherein said reagent or series of reagents, distinguishes between wildtype ANXA5 gene regulatory sequences and an ANXA5 gene regulatory sequence comprising at least one mutation as defined in the present invention.

In one embodiment, the method comprises the following steps: In the first step of the method the genomic DNA sample is isolated from sources such as cells or cellular components which contain DNA, sources of DNA comprising, for example, ovarian tissue, breast tissues as well as blood, plasma, sputum, lymphatic fluid, lymphatic tissue, duct cells, ductal lavage fluid, nipple aspiration fluid and combinations thereof. Also envisaged are probes derived from buccal swabs. Extraction may be by means that are standard to one skilled in the art, these include the use of detergent lysates, sonification and vortexing with glass beads. Once the nucleic acids have been extracted the genomic double stranded DNA is used in the analysis.

Details of corresponding methods of the present invention are given in the appended examples. In one embodiment the DNA may be cleaved prior to the next step of the method, this may be by any means standard in the state of the art, in particular, but not limited to, with restriction endonucleases. The appended examples provide for one technique where BamHI is employed to detect at least one point mutation as defined herein.

Also, PCR methods are envisaged as mentioned above. Fragments (e.g. fragments comprising preferably about 100 by or most preferably at least 50 bp) of the genomic DNA are amplified, using sets of primer oligonucleotides, and a preferably heat-stable, polymerase. Because of statistical and practical considerations, preferably more than six different fragments having a length of 50-2000 base pairs (bp) are amplified. However, fragments of at least 50 by may be amplified. The amplification of several DNA segments can be carried out simultaneously in one and the same reaction vessel. Usually, the amplification is carried out by means of said polymerase chain reaction (PCR). Again, corresponding examples are given in the experimental part.

The design of such primers is known to one skilled in the art. These should include at least two oligonucleotides whose sequences are each reverse complementary or identical to an at least 18 base-pair long segment of the following base sequences specified in the appendix: SEQ ID NO 1 to 4 and comprising at least one mutation as provided herein. Said primer oligonucleotides are preferably characterised in that they are capable of detecting at least one mutation as provided here. In a particularly preferred embodiment of the method, the sequence of said primer oligonucleotides are designed so as to selectively anneal to and amplify, only the specific DNA of interest (comprising said at least one mutation), thereby minimising the amplification of background or non relevant DNA. In the context of the present invention, background DNA is taken to mean genomic DNA which does not have a relevant mutation in the ANXA5 promoter region or which is not related to the ANXA5 promoter. Preferred primers are given in the appended examples and comprise, inter alia, the primers as shown in SEQ ID NO: 5 to 16.

According to the present invention, it is also envisaged that at least one primer oligonucleotide is bound to a solid phase during amplification. The different oligonucleotide and/or PNA-oligomer sequences can be arranged on a plane solid phase in the form of a rectangular or hexagonal lattice, the solid phase surface preferably being composed of silicon, glass, polystyrene, aluminum, steel, iron, copper, nickel, silver, or gold, it being possible for other materials such as nitrocellulose or plastics to be used as well.

The fragments obtained by means of the amplification may carry a directly or indirectly detectable label. Preferred are labels in the form of fluorescence labels, radionuclides, or detachable molecule fragments having a typical mass which can be detected in a mass spectrometer.

In the next step the nucleic acid amplificates are analysed in order to determine the mutation status of the genomic DNA.

In one embodiment of the herein disclosed methods the mutation status of the ANXA5 promoter may be determined by means of hybridisation analysis. In this embodiment the amplificates are, inter alia, hybridised to an array or a set of oligonucleotides and/or PNA probes. In this context, the hybridisation may take place in the manner described as follows.

The set of probes used during the hybridisation is preferably composed of at least 4 oligonucleotides or PNA-oligomers. In the process, the amplificates serve as probes which hybridise to oligonucleotides previously bonded to a solid phase. The non-hybridised fragments are subsequently removed. Said oligonucleotides contain at least one base sequence having a length of 10 nucleotides which is reverse complementary or identical to a segment of the nucleic acid molecule comprising at least one mutation as defined herein to a fragment of said nucleic acid molecule, whereby said fragment comprises at least one mutation as defined herein or whereby said fragment relates to a fragment of the ANXA5 promoter.

The non-hybridised amplificates are then removed. In the final step of the method, the hybridised amplificates are detected. In this context, it is preferred that labels attached to the amplificates are identifiable at each position of the solid phase at which an oligonucleotide sequence is located.

In a preferred embodiment of the method the mutation status of the ANXA5 promoter may be determined by means of oligonucleotide probes that are hybridised to the treated DNA concurrently with the PCR amplification primers.

A particularly preferred embodiment of this method is the use of fluorescence-based Real Time Quantitative PCR (Heid et al., Genome Res. 6:986-994, 1996) employing a dual-labelled fluorescent oligonucleotide probe (TaqMan™ PCR, using an ABI Prism 7700 Sequence Detection System, Perkin Elmer Applied Biosystems, Foster City, Calif.). The TaqMan™ PCR reaction employs the use of a nonextendible interrogating oligonucleotide, called a TaqMan™ probe, which is designed to hybridise to a GpC-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide.

The oligomer probes as well as the primers according to the present invention constitute important and effective tools which, for the first time, make it possible to ascertain specific parameters during the analysis and monitoring of human pregnancy. Said oligonucleotides allow the improved treatment and monitoring of women in danger of pregnancy loss/wastage.

The Figures show:

FIG. 1: Sequence chromatograms of Bam HI ANXA5 promotor allele variants. N/N=wildtype, M/N=heteroyzgote, M/M=homozygote for the BamHI allele.

FIG. 2: Structure of the ANXA5 core promotor region. The region boundaries are marked with vertical bars and are numbered according to the position of the first transcription start point (tsp1). Untranslated exon 1 is shaded in gray. Transcription factor consensi are in small print and abbreviations of corresponding transcription factors are italisized over the sequence rows. NotI and BamHI restriction sites are underlined and the sequence of the Z-DNA stretch in the promotor is in italics. Nucleotides marking transcription start points (tsp) are underlined. Regions important for promotor function (motifs A and B accordingly) occupy nucleotide positions 295-311 and 328-337. Nucleotides changed in the BamHI⁻ haplotype are bolded and substituting nucleotides are indicated in bold capital letters over the matching respective positions.

Figure 3:
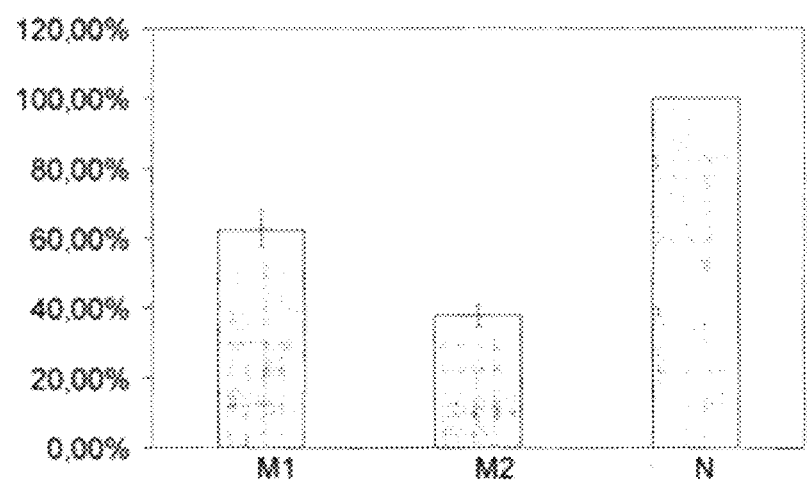

FIG. 3. Measurements of the annexin A5 promotor variant activities (luciferase reporter gene assays). N nominates the wild type promotor sequence, which is normalized as 100% activity. M1 contains the nucleotide changes 1A→C and 27T→C, and the M2 variant harbors all four substitutions (−19G→A, 1A→C, 27T→C and 76G→A), characteristic of the BamHI⁻ ANXA5 promotor variant.

Figure 4:
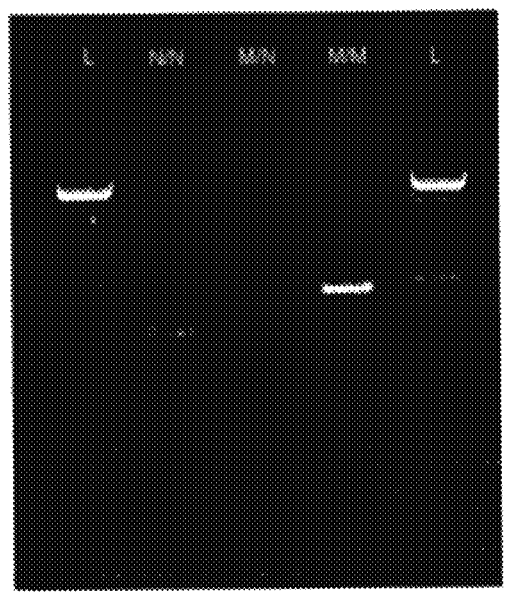

FIG. 4. BamHI restriction digest for detection of BamHI⁻ ANXA5 promotor allele. Lane 1, PCR product of a wild type (N/N) genotype; lane 2, (M/N), heterozygosity for the BamHI⁻ allele; lane 3, (M/M), homozygosity for the BamHI⁻ variant; L is a size standard (100 by ladder, MBI Fermentas).

The examples illustrate the invention.

EXAMPLE I

Materials and Methods used in the Present Invention

Patients with Recurrent Pregnancy Loss

Seventy patients of North European origin with a condition of repeated pregnancy loss (more than two fetal losses), who were referred for genetic counseling to the Institute of Human Genetics, University Clinics Muenster, were examined for mutations in the ANXA5 gene.

These patients were pre-screened for the PTm and factor V Leiden mutations and found to be non-carriers.

The study complies with the ethical guidelines of the institutions involved. Informed consent was obtained from all subjects examined.

Sequence Analysis of the ANXA5 Gene

The analysis was performed on the entire coding sequence of ANXA5, along with 60-80 by of the flanking introns and the gene promoter region (the first untranslated exon and about 270 bp upstream in the 5' UTR). After PCR amplification of the relevant genomic regions, direct sequencing of amplicons was performed using an automated sequencer, ABI PRISM® 3700 DNA Analyzer (ABI/Perkin-Elmer, Weiterstadt, Germany).

Control Group and Patients Screening

The population frequency of the M1 and M2 promoter variant alleles was analyzed in the sample of 533 anonymized female control persons below reproductive age, of Northwest German origin, as well as in the above described patient group of 70 groups. M2 alleles (BamHI⁻ variants) were determined through BamHI digestion of amplicons comprised of 436 by ANXA5 promotor region sequence. Heterozygous and homozygous BamHI⁻ carrierships were confirmed through sequencing of respective amplicons in all BamHI⁻ patient and control subjects. BamH⁺ carriers were further screened for the presence of 1A→C and 27T→C mutations (M1 haplotype), using allele specific PCR amplification with primers 5' CCCTGGCGGGGGTGGGA 3' (SEQ ID NO: 11) and 5' CCCTGGCGGGGGTGGGC 3' (SEQ ID NO: 12) with reverse primer 5' GTTGTGGG-TAAATCCAGCGCA 3' (SEQ ID NO: 13), discriminating the 1A and 1C variants and primers 5' CCGGGCAGGGC-CGGGGT 3' (SEQ ID NO: 14) and 5' CCGGGCAGGGC-CGGGGC 3' (SEQ ID NO: 15) with reverse primer 5' GAACCGGGACACAGAAAC 3' (SEQ ID NO: 16), discriminating the 27T and 27C variants. Amplicons of all heterozygous and homozygous M1 carriers determined by allele specific PCR amplification in the patient and control groups were further sequenced to confirm the 1A→C and 27T→C mutations. In the control group M1 and M2 genotypes were determined through sequencing of the relevant promotor region.

Haplotype Determination for the ANXA5 M1 and M2 (BamHI⁻) Alleles

Amplicons of patients or control subjects containing 436 by of the ANXA5 promoter and characterized with two (1A→C and 27T→C) or four (−19G→A,1A→C, 27T→C and 76G→>A) mutations were cloned in the pGL3-Basic vector (Promega, Freiburg, Germany). Ten insert carrying clones of amplicons containing the four mutations were selected at random and plasmid DNA was hydrolyzed with BamHI and inserts of BamHI⁺ and BamHI⁻ clones were sequenced in both directions. Cloned inserts of amplicons containing the two (1A→C and 27T→C) mutations were directly sequenced in both directions from ten randomly selected clones.

Reporter Gene Assays

Analyses were performed in parallel for the M1 and M2 (BamHI⁻) ANXA5 promotor variants, to assess their relevance for the expression of the gene. A luciferase gene, contained in the pGL3-Basic vector was selected as reporter. A beta-galactosidase gene under the strong CMV promotor served as internal standard (BD Biosciences Clontech, Heidelberg). The constructs were expressed in HeLa cells and reporter activities were measured. The measurements were repeated each 3 times, for five independent construct expressions and all values were presented as ratios to estimated beta-galactosidase activity.

Statistical Analysis

Genotypic and allelic distributions in cases and controls were compared using $\chi^2$ tests and logistic regression analysis. Computer-based simulation methods were used to test departures in the genotypic frequencies from those expected under Hardy-Weinberg equilibrium, as well as for building 95% confidence intervals for estimates of gene frequencies and odds ratios calculation. The analyses were conducted with software from the SAS v8 library and the web-based EpiMax Calculator; see, inter alia, www.healthstrategy.com/epiper1/epiper1.htm. However, other commonly used software may be used as provided by, inter alia, ISI (International Statistical Institute).

EXAMPLE II

Identification of Specific ANXA5 Promoter Mutations

Through systematic mutation screening of exons together with exon-intron boundaries and 270 by of the 5' untranslated region of the gene, four consecutive nucleotide substitutions in the ANXA5 promoter were identified in the patient group. These are numbered starting from the first transcription start point of the gene, tsp1, (+1). These substitutions are as follows: −19G→A, 1A→C, 27T→C and 760→A. Alternative numbering is provided herein and relate to the sequences provided herein. The four changes together or only two of them (1A→C and 27T→C) are inherited as haplotypes, i.e. either all four of them are on one and the same DNA strand, M2 haplotype, or the two "middle" changes (1A→C and 27T→C) are found on the same DNA strand, M1 haplotype (allele subcloning and sequencing results). The fourth substitution, 76G→A, changes an existing BamHI restriction site, the resulting mutant promotor allele that contains all four nucleotide replacements was named "BamHI⁻ allele". FIG. 1 represents sets of chromatograms of the sequence of an amplicon in wildtype (−/−, i.e. Bam HI⁺/Bam HI⁺), heterozygous (Bam HI⁺/BamHI⁻) and homozygous (BamHI⁻/BamHI⁻) carriers of the BamHI⁻ allele. The 76G→A substitution is well visible. In addition, the distribution of M1 and M2 alleles in patients and in a control group of 500 individuals (see under Materials and Methods, control group and patients screening) was estimated. The results of M1 and M2 allele distributions in patients and controls are summarized in the following Table 1. In first series of statistical analysis with 500 female control subjects with no recorded history of recurrent pregnancy losses (super-controls), a significant departure from Hardy-Weinberg equilibrium regarding M2 allele presentation was observed in this group (D=0.026, 95% CI: 0.016-0.038). This deviation is confirmed both using a $\chi^2$ test ($\chi^2$=105.2, d.f.=2, p<0.0001) and using a simulation test (p-value<0.0001). The data suggest that in the control sample heterozygotes are underrepresented (31 observed versus −49 predicted under H-W), whereas homozygotes for BamHI⁻ are overrepresented (observed 10, predicted ~2).

TABLE 1

Genotype distributions of the M1 and M2 ANXA5 promoter alleles in patients and controls.

| Genotype | Patients | | Controls | | OR | CI |
| --- | --- | --- | --- | --- | --- | --- |
| | Observed | Expected | Observed | Expected | | |
| N/N | 45 (64.3%) | 44.8 | 415 (77.8%) | 413.3 | 1.000 | n.a. |
| N/M1 | 6 (8.6%) | 6.4 | 35 (6.6%) | 47.8 | 1.581 | 0.563-4.208 |
| M1/M1 | 1 (1.5%) | 0.2 | 1 (0.2%) | 1.5 | 9.222 | 0.249-342.136 |

TABLE 1-continued

Genotype distributions of the M1 and M2 ANXA5 promoter alleles in patients and controls.

| Genotype | Patients | | Controls | | OR | CI |
|---|---|---|---|---|---|---|
| | Observed | Expected | Observed | Expected | | |
| N/M2, M1/M2[a] | 16 (22.8%) | 17.2 | 77 (14.4%) | 69 | 1.916[b] | 0.983-3.703 |
| M2/M2 | 2 (2.8%) | 1.4 | 5 (1%) | 1.4 | 3.689 | 0.481-22.321 |
| Total | 70 | 70 | 533 | 533 | | |

Expected: genotype frequency expected at Hardy-Weinberg equilibrium;
OR: odds ratio with respect to genotype N/N;
CI: 95% confidence interval for the odds ratio;
[a]genotype M1/M2 was only observed in five control individuals;
[b]$\chi^2$ = 3.619, 1 d.f., p = 0.057.

EXAMPLE III

Analysis of Nucleotide Changes and Receptor Gene Assays

All observed nucleotide changes in the annexin A5 promoter change transcription factor consensus sites, or nucleotides in their direct proximity (+/−1 nucleotide). FIG. 2 depicts the structure of the ANXA5 promotor with highlighted transcription factor binding sites. The −19 G→A substitution is adjacent to the gGCCc consensus of the MTF-I transcription factor. The transcription start point, tspl is changed 1A→C in the promoter haplotype, which also lies in a close proximity to the HNF-3 consensus. The 27T→C substitution breaks an SpI consensus and the 76G→A variant changing the BamHI restriction site is in direct proximity to an AP4/MED-1 consensus, "motif B", shown to be indispensable for ANXA5 promoter activity [Carcedo et al., 2001].

To investigate whether these nucleotide changes, associated in haplotypes would affect the activity of the ANXA5 major transcription regulatory region, we performed reporter gene assays on both, M1 and M2 variants (see under Materials and Methods, Reporter gene assays). FIG. 3 summarizes the results of activity measurements. Every measurement was taken in triplicate. Data obtained show drastic reduction of the ANXA5 promoter activity when all four nucleotide substitutions (BamHI− allele) are present. Thus, the M2 promoter activity amounts to 37-42% of the normal ANXA5 promoter activity, measured on the normal allele. In contrast, the M1 allele renders a reduced promotor activity of 57-62%. The observed variation of measured activities is inborn to the procedure applied and stems from varying physiological conditions of expressing cultured cells.

EXAMPLE IV

Statistical Analysis

From patients comprising a high risk pregnancy group 70 subjects were selected in which no thrombophilic factor V Leiden or prothrombin PTm mutations were identified. M1 and M2 promoter allele genotypes were compared in the patient group and control population (Table 1). In the controls genotypes were found to be at Hardy-Weinberg equilibrium. In the high-risk group, genotype frequencies appeared to be at their Hardy-Weinberg equilibrium values (D=0.01, 95% CI: −0.012-0.043), which was confirmed with the $\chi^2$ test ($\chi^2$=0.58, d.f.=2, N.S.) and with the simulation test (p-value<0.131).

For the M1 haplotype it was found in a first analysis that for M1 carriers, the association between genotype and disease status is of borderline significance ($\chi^2$=3.905, 1 df, p=0.048). The odds ratio (OR) is 0.423, with a wide 95% confidence interval of 0.172-0.994. Carriership of M1 in either homozygous or heterozygous state is either inconsequential or weakly protective against recurrent abortion.

For the M2 (BamHI− allele) carriership, the association between genotype and disease status is highly significant ($\chi^2$=18.455, 1 df, p=1.7×10$^{-5}$). The odds ratio equals 3.875 (nearly fourfold), with a 95% confidence interval of 1.980-7.542. Thus, M2 is a strong risk factor in that carriers face a four times higher relative risk of recurrent abortion than non-carriers.

Differences between homozygosity and heterozygosity are not conclusive. A possible effect was seen for M2, where heterozygosity N/M2 apparently entailed a higher risk (OR=4.083) than homozygosity (OR=1.582). However, the confidence intervals for the odds ratios widely overlap (1.961-8.457 for N/M2 versus 0.231-8.057 for M2/M2). The observed departure from Hardy-Weinberg equilibrium regarding M2 allele presentation in the control group could be indeed an additional indication of the role of this ANXA5 promotor variant for recurrent pregnancy loss, since selected control subjects have had no recorded pregnancy problems. Comparing with the general population, the risk of carrying the M2 haplotype might be lower, considering that about 10% to 15% of all women suffer from pregnancy losses.

In a further analysis, the following results, which are completely in line with the results provided herein above, are found:

For the M1 haplotype it was found that for M1 heterozygotes, the association between genotype and disease status is of borderline significance ($\chi^2$=0.511, 1 df, p=0.475). The odds ratio (OR) is 1.581, with a wide 95% confidence interval of 0.563-4.208. It was therefore concluded that carriership of M1 in heterozygous state is rather inconsequential for recurrent abortion and the number of homozygotes in patients and controls is too low to make a justified conclusion.

For the M2 (BamHI− allele) carriership, the association between genotype and disease status is significant ($\chi^2$=4.763, 1 df, p=0.029). The odds ratio equals 2.024, with a 95% confidence interval of 1.068-3.810. Thus, M2 is a risk factor in that carriers face about two times (1.840) higher relative risk of recurrent abortion than non-carriers.

Numbers in the cases group are too small to test for any interaction between haplotypes, or for differences between homozygosity and heterozygosity. A possible effect was seen for M2, where homozygosity N/M2 apparently entailed a higher risk (OR=3.689) than heterozygosity (OR=I.916). However, the confidence interval for the M2/M2 odds ratio is rather wide (0.481-22.321), so that such a conclusion would not be justified from a statistical point of view. Since the control group is a representative sample of the population from Northwest Germany, the estimated risk of carrying the M2 haplotype should be indicative of the population risk, considering that about 10% of all women suffer from pregnancy losses.

EXAMPLE V

Analytical Procedures

The proposed analytical procedure for detection of the M2 (BamHI⁻) allele may comprise consecutive steps:
1. PCR reaction;
2. Barn HI restriction digest of an aliquot of the PCR product; and
3. Gel electrophoresis of the restriction digest products The template for 1. is human genomic DNA from peripheral blood. The products of 2. are subjected to electrophoretic separation in an agarose gel and visualized with ethidium bromide staining.
1. PCR reaction:

In 25 µl volume on 100 ng genomic DNA. Composition of the reaction mix and reaction buffer may be different and depend on the Tag polymerase supplier. Oligonucleotide amplification primers, 20 pM each:

```
ANX5.P.F:
                                    (SEQ ID NO: 22)
5' CCGAGCCCTGGACAGCTCCCCA 3'

ANX5.ex1.R:
                                    (SEQ ID NO: 23)
5' CCAGACTGTGGGACCCAAGT 3'
``` amplicon size: 436 bp. Cycling conditions: (94° C., 45 s); 30×[(94° C., 30 s); (60° C., 30 s); 68° C., 1 min)]; (68° C., 7 min); (15° C., ∞);
2. Restriction digest:

In 10 µl volume, with 1 U of Bam HI restriction enzyme (various suppliers). Restriction digest on 5-7 µl of the PCR product (reaction 1), on 37° C., 18-20 hours.
3. Agarose gel electrophoresis:

The products of (2) are mixed with 2 µl 6x gel loading buffer and are then loaded on 1.5% agarose gels. The gels run in 1×TAE buffer, constant voltage (6V/cm) for 30 min. The separated and ethidium bromide stained reaction products are visualized on a transilluminator (384 nm) and can be documented. If the BamHI restriction site is intact (wildtype DNA), in homozygous condition two bands can be seen (336 and 100 bp), and three bands in heterozygotes with a BamHI⁻ allele (an additional 436 by band, non-digested amplicon). When the BamHI restriction site is not intact in homozygotes, there is only the 436 by band to be seen. FIG. 4 shows a gel picture of BamHI digested PCR products from patients and control individuals.

| | diagnostic bands | | |
|---|---|---|---|
| genotypes | 436 bp | 336 bp | 100 bp |
| BamHI⁺/BamHI⁺ homozygote | − | + | + |
| BamHI⁺/BamHI⁻ heterozygote | + | + | + |
| BamHI⁻/BamHI⁻ homozygote | + | − | − |

The analytical procedure we developed is able to discriminate M2 (Bam HI) allele carriers (heteroyzgotes and homozygotes), who possess about four fold (3.875) higher relative risk of recurrent abortion compared to non-carriers, as measured among healthy, female control subjects with no previously reported pregnancy problems (see under IV, Statistical analysis). Statistically differences on the relative risk rates of individuals, heterozygous or homozygous for the M2 (BamHI⁻) allele have not been established.

What is claimed is:

1. A nucleic acid molecule either (a) covalently attached to a fluorescent label or (b) fixed to a solid phase, the solid phase comprising a material selected from the group consisting of plastic, silicon, glass, polystyrene, aluminum, steel, iron, copper, nickel, silver, gold, nitrocellulose, and nylon, the nucleic acid molecule having a sequence with 95% or greater identity to SEQ ID NO: 2 over its full length or having a sequence with 95% or greater identity to SEQ ID NO: 4 over its full length, the nucleic acid molecule comprising at least one point mutation, whereby said at least one point mutation (substitution) is selected from the group consisting of (i) a point mutation G to A at a position which corresponds to nucleotide 186 of SEQ ID NO: 2 or nucleotide 190 of SEQ ID NO: 4; or (ii) a point mutation A to C at a position which corresponds to nucleotide 203 of SEQ ID NO: 2 or nucleotide 209 of SEQ ID NO: 4.

2. The nucleic acid molecule of claim 1, having point mutation G to A at position 186 of SEQ ID NO: 2 or nucleotide 190 of SEQ ID NO: 4.

3. The nucleic acid molecule of claim 1 having point mutation A to C at position 203 of SEQ ID NO: 2 or nucleotide 209 of SEQ ID NO: 4.

4. The nucleic acid molecule of claim 1, further comprising (i) a point mutation T to C at a position which corresponds to nucleotide 229 of SEQ ID NO: 2, or (ii) a point mutation T to C at a position which corresponds to nucleotide 235 of SEQ ID NO: 4.

5. The nucleic acid molecule of claim 1, further comprising (i) a point mutation G to A at a position which corresponds to nucleotide 276 of SEQ ID NO: 2, or (ii) a point mutation G to A at a position which corresponds to nucleotide 284 of SEQ ID NO: 4.

6. The nucleic acid molecule of claim 3 comprising the following sequences:

(i)
                                                    (SEQ ID NO: 17)
TGCGGTTGGGGC;

(ii)
                                                    (SEQ ID NO: 19)
GCTGGCGTTTCCGTTGCTTGGATCAGTCTAGGTGCAGCTGC;
and (iii)
                                                    (SEQ ID NO: 20)
GGATCC.

7. The nucleic acid molecule of claim 2 comprising the following sequences:

(iii)
                                                    (SEQ ID NO: 19)
GCTGGCGTTTCCGTTGCTTGGATCAGTCTAGGTGCAGCTGC;
and (iv)
                                                    (SEQ ID NO: 20)
GGATCC.

8. The nucleic acid molecule of claim 1 comprising:

(i) a point mutation G to A at a position which corresponds to nucleotide 186 of SEQ ID NO: 2;

(ii) a point mutation A to C at a position which corresponds to nucleotide 203 of SEQ ID NO: 2;

(iii) a point mutation T to C at a position which corresponds to nucleotide 229 of SEQ ID NO: 2; and (iv) a point mutation G to A at a position which corresponds to nucleotide 276 of SEQ ID NO: 2.

9. The nucleic acid molecule of claim 1 which is operatively linked to a gene encoding for a marker protein, a signal protein or a reporter gene.

10. The nucleic acid molecule of claim 1 which is DNA, RNA or PNA.

11. A vector comprising (a) a nucleic acid molecule having a sequence with 95% or greater identity to SEQ ID NO: 2 over its full length or having a sequence with 95% or greater identity to SEQ ID NO: 4 over its full length, the nucleic acid molecule comprising at least one point mutation, whereby said at least one point mutation (substitution) is selected from the group consisting of (i) a point mutation G to A at a position which corresponds to nucleotide 186 of SEQ ID NO: 2 or nucleotide 190 of SEQ ID NO: 4; or (ii) a point mutation A to C at a position which corresponds to nucleotide 203 of SEQ ID NO: 2 or nucleotide 209 of SEQ ID NO: 4; and (b) a nucleic acid having a sequence that is heterologous to (a).

12. The vector of claim 11 which is an expression vector or a gene transfer vector.

13. A nucleic acid molecule either (a) covalently attached to a fluorescent label or (b) fixed to a solid phase, the solid phase comprising a material selected from the group consisting of plastic, silicon, glass, polystyrene, aluminum, steel, iron, copper, nickel, silver, gold, nitrocellulose, and nylon, wherein the nucleic acid molecule is all or a portion of SEQ ID NO: 2 and the nucleic acid having haplotype M1 or M2, wherein haplotype M1 has at position 203 a substitution from A to C and at position 229 a substitution from T to C, and wherein haplotype M2 has at position 186 a substitution from G to A, at position 203 a substitution from A to C, at position 229 a substitution from T to C and at position 276 a substitution from G to A.

14. A nucleic acid molecule either (a) covalently attached to a fluorescent label or (b) fixed to a solid phase, the solid phase comprising a material selected from the group consisting of plastic, silicon, glass, polystyrene, aluminum, steel, iron, copper, nickel, silver, gold, nitrocellulose, and nylon, wherein the nucleic acid molecule is an oligomer having a length of at least 28 nucleotides capable of hybridizing under stringent conditions to:
  a portion of SEQ ID NO: 1, the oligomer having:
    (i) a point mutation G to A at a position which corresponds to nucleotide 1259 of SEQ ID NO: 1;
    (ii) a point mutation A to C at a position which corresponds to nucleotide 1276 of SEQ ID NO: 1;
    (iii) a point mutation T to C at a position which corresponds to nucleotide 1302 of SEQ ID NO: 1; or
    (iv) a point mutation G to A at a position which corresponds to nucleotide 1349 of SEQ ID NO: 1; or
  a portion of SEQ ID NO: 2, the oligomer having:
    (i) a point mutation G to A at a position which corresponds to nucleotide 186 of SEQ ID NO: 2;
    (ii) a point mutation A to C at a position which corresponds to nucleotide 203 of SEQ ID NO: 2;
    (iii) a point mutation T to C at a position which corresponds to nucleotide 229 of SEQ ID NO: 2; or
    (iv) a point mutation G to A at a position which corresponds to nucleotide 276 of SEQ ID NO: 2; or
  a portion of SEQ ID NO: 3, the oligomer having:
    (i) a point mutation G to A at a position which corresponds to nucleotide 243 of SEQ ID NO: 3;
    (ii) a point mutation A to C at a position which corresponds to nucleotide 262 of SEQ ID NO: 3;
    (iii) a point mutation T to C at a position which corresponds to nucleotide 288 of SEQ ID NO: 3; or
    (iv) a point mutation G to A at a position which corresponds to nucleotide 337 of SEQ ID NO: 3; or
  a portion of SEQ ID NO: 4, the oligomer having:
    (i) a point mutation G to A at a position which corresponds to nucleotide 190 of SEQ ID NO: 4;
    (ii) a point mutation A to C at a position which corresponds to nucleotide 209 of SEQ ID NO: 4;
    (iii) a point mutation T to C at a position which corresponds to nucleotide 235 of SEQ ID NO: 4; or
    (iv) a point mutation G to A at a position which corresponds to nucleotide 284 of SEQ ID NO: 4.

15. The nucleic acid of claim 14 which is an oligonucleotide or a peptide nucleic acid (PNA)-oligomer.

16. A composition comprising an oligomer set, wherein the oligomer set consists essentially of two oligomers that allow polymerase chain reaction amplification of a DNA fragment comprising at least from nucleotide 1259 to nucleotide 1349 of SEQ ID NO: 1 the two oligomers including a forward oligomer and a reverse oligomer either or both (a) covalently attached to a fluorescent label or (b) fixed to a solid phase, the solid phase comprising a material selected from the group consisting of plastic, silicon, glass, polystyrene, aluminum, steel, iron, copper, nickel, silver, gold, nitrocellulose, and nylon, the forward oligomer and reverse oligomer each having a length of at least 15 nucleotides, wherein the forward oligomer is capable of hybridizing to:
  a portion of SEQ ID NO: 1 and wherein the forward and reverse oligomers allow the polymerase chain reaction amplification of a DNA fragment comprising at least from nucleotide 1259 to nucleotide 1349 of SEQ ID NO: 1, wherein the forward or reverse oligomer has;
    (i) a point mutation G to A at a position which corresponds to nucleotide 1259 of SEQ ID NO: 1;
    (ii) a point mutation A to C at a position which corresponds to nucleotide 1276 of SEQ ID NO: 1;
    (iii) a point mutation T to C at a position which corresponds to nucleotide 1302 of SEQ ID NO: 1; or
    (iv) a point mutation G to A at a position which corresponds to nucleotide 1349 of SEQ ID NO: 1; or,
  a portion of SEQ ID NO: 2 and wherein the forward and reverse oligomers allow the polymerase chain reaction amplification of a DNA fragment comprising at least from nucleotide 186 to nucleotide 276 of SEQ ID NO: 2, wherein the forward or reverse oligomer has;
    (i) a point mutation G to A at a position which corresponds to nucleotide 186 of SEQ ID NO: 2;
    (ii) a point mutation A to C at a position which corresponds to nucleotide 203 of SEQ ID NO: 2;
    (iii) a point mutation T to C at a position which corresponds to nucleotide 229 of SEQ ID NO: 2; or
    (iv) a point mutation G to A at a position which corresponds to nucleotide 276 of SEQ ID NO: 2; or,
  a portion of SEQ ID NO: 3 and wherein the forward and reverse oligomers allow the polymerase chain reaction amplification of a DNA fragment comprising at least from nucleotide 243 to nucleotide 337 of SEQ ID NO: 3, wherein the forward or reverse oligomer has;
    (i) a point mutation G to A at a position which corresponds to nucleotide 243 of SEQ ID NO: 3;
    (ii) a point mutation A to C at a position which corresponds to nucleotide 262 of SEQ ID NO: 3;
    (iii) a point mutation T to C at a position which corresponds to nucleotide 288 of SEQ ID NO: 3; or
    (iv) a point mutation G to A at a position which corresponds to nucleotide 337 of SEQ ID NO: 3; or
  a portion of SEQ ID NO: 4 and wherein the forward and reverse oligomers allow the polymerase chain reaction amplification of a DNA fragment comprising at least from nucleotide 190 to nucleotide 284 of SEQ ID NO: 4, wherein the forward or reverse oligomer has;
    (i) a point mutation G to A at a position which corresponds to nucleotide 190 of SEQ ID NO: 4;
    (ii) a point mutation A to C at a position which corresponds to nucleotide 209 of SEQ ID NO: 4;
    (iii) a point mutation T to C at a position which corresponds to nucleotide 235 of SEQ ID NO: 4; or
    (iv) a point mutation G to A at a position which corresponds to nucleotide 284 of SEQ ID NO: 4, wherein
  (a) the forward oligomer has SEQ ID NO: 8 or SEQ ID NO: 9 and the reverse oligomer has SEQ ID NO: 10 or SEQ ID NO: 13;
  (b) the forward oligomer has SEQ ID NO: 11, SEQ ID NO: 21, or SEQ ID NO: 12 and the reverse oligomer has SEQ ID NO: 13 or SEQ ID NO: 10;
  (c) the forward oligomer has SEQ ID NO: 14 or SEQ ID NO: 15 and the reverse oligomer has SEQ ID NO: 16 or SEQ ID NO: 7; or
  (d) the forward oligomer has SEQ ID NO: 5 or SEQ ID NO: 6 and the reverse oligomer has SEQ ID NO: 7 or SEQ ID NO: 16.

17. A kit comprising the oligomer composition of claim 16 for diagnosing or detecting a predisposition for or a tendency to pregnancy loss.

18. The oligomer composition of claim 16 wherein the forward oligomer is selected from the group consisting of:
  (i) a forward oligomer capable of hybridizing under stringent conditions to a portion of SEQ ID NO: 2 having a point mutation G to A at a position which corresponds to nucleotide 186 of SEQ ID NO: 2;
  (ii) a forward oligomer capable of hybridizing under stringent conditions to a portion of SEQ ID NO: 2 having a point mutation A to C at a position which corresponds to nucleotide 203 of SEQ ID NO: 2;
  (iii) a forward oligomer capable of hybridizing under stringent conditions to a portion of SEQ ID NO: 2 having a point mutation T to C at a position which corresponds to nucleotide 229 of SEQ ID NO: 2; and iv) a forward oligomer capable of hybridizing under stringent conditions to a portion of SEQ ID NO: 2 having a point mutation G to A at a position which corresponds to nucleotide 276 of SEQ ID NO: 2, wherein the forward oligomer is selected from the group consisting of:

(i) the forward oligomer having SEQ ID NO: 9;
(ii) the forward oligomer having SEQ ID NO: 12;
(iii) the forward oligomer having SEQ ID NO: 15; and
(iv) the forward oligomer having SEQ ID NO: 6.

19. The nucleic acid molecule of claim 1 further comprising a sequence with 95% or greater identity to SEQ ID NO: 1 over its full length.

20. The nucleic acid molecule of claim 1 further comprising a sequence with 95% or greater identity to SEQ ID NO:3 over its full length.

21. The nucleic acid molecule of claim 1 wherein the nucleic acid molecule is covalently attached to a fluorescent label, and the fluorescent label is a cyanine dye.

22. The nucleic acid molecule of claim 21 wherein the cyanine dye is Cy3 or Cy5.

23. The vector of claim 11 wherein the heterologous nucleic acid sequence (b) is selected from the group consisting of a promoter, a polylinker, a termination signal, an origin of replication, and a selection marker.

* * * * *

SEQUENCE LISTING

```
<160> NUMBER OF SEQ ID NOS: 23

<210> SEQ ID NO 1
<211> LENGTH: 1732
<212> TYPE: DNA
<213> ORGANISM: Homo sapiens

<400> SEQUENCE: 1
tctagaacac tgcatctagt gtcgcaaact tgtcctcttg cccctctgc cctggcacct      60 tccctcccca caccagtaag tctgagaagg tccctgtgtc ttctactttt cctttccag    120 catatggaga caaaagtgat tatatcccgg atgctaatcc gccatgttga cctttaataa   180
ccccagtccc atgaatacct cctgattcct aggattttt ttttaaactg tccttagcat    240
aagaacatgt caaccttgat gctattgccc acattgtagg ctatgaagca tacggcattc   300
tcacctgttc cggaggctgc ctttaattgt cttgcacaga gcagtatact ctttccttac   360
ggtatataag gccagggtct ggggagtaac agtgcagaaa tttatctgct tgccgccgcc   420
caaggccacg cttctgtcta ccacatcctc caatagcacc cctattacct acagactgga   480
```

```
tttgtctgtc tcgttctttg gtttcttgac tccttcgcgt ttgggggctg ctttgcatat      540
aaagcccttt cacagaacac agcaccatgc tagtacaata cgctgtagat tctccctccc      600
tccccctctc tctcatatac tcatatatct tatgttgaac caatatgagg cattgctcaa      660
atttaagtca tattaaagtt ctaggctagt tttgaaaaca gaaactgatt ggaagcagag      720
gttttcaaat agcccacata cgctactaga aggctgtaca tttaagagag ggccatctag      780
gaagcaataa taggcattaa acaacaata aacaacaaa acaaaacaga aacaaaaaca       840
acttgggaaa cggccctcct ttcacgtttt ttctatccca tcgacaaagg cgcgctgtcc      900
ttagctgcga tgattttgtc tcgcctccaa aaagacgccc acgcactatg ttgagcaccc      960
aagtgaggct acggttcctg cggtcacaga gggcaggag gctcaagcac ctccaaaacc      1020
ccgagccctg acagctccc caggccctc ccgcggcgcg aggacaagag gtctccgggg      1080
ccctcggggg agcggcgcct cctcctggtt ccagcagctc tgcgccgctc cccacccagg     1140
cccgcgagac cagcgggaca gtccgcgccg ggagaccaac tgggacgagc cgcgacccac     1200
gcaggcgcgc tgaggccggg gcaggggcgg gcccggctgg cgcggccggc tgcggttggg     1260
gctggcgggg gtgggacggg ccaagccggg caggccgggg gtggggcgct ggcgtttccg     1320
ttgcttggat cagtctaggt gcagctgcgg atccttcagc gtctgcatct cggcgtcgcc     1380
ccgcgtaccg tcgcccggct ctccgccgct ctccgggggg ttcggggcac ttgggtccca     1440
cagtctgggt gagtggtcgc agcccgggga ggggctcct tctggagagg agagcgtggt      1500
cgcggggcac tggattcgcg cggacgctcg gccgagagct gtcccggtag ctgcgagagg     1560
gcgggtcggc ccgtggcggc gtccgggctg tctgagcgcg ccggtccccg cggacctgcg     1620
cttggggagg gcacgagttg caaatggcgc gctaagcccg aggtttcttc tcttttgcag     1680
tcctgcttca ccttcccctg acctgagtag tcgccatggc acaggtaagg cc             1732

<210> SEQ ID NO 2
<211> LENGTH: 281
<212> TYPE: DNA
<213> ORGANISM: Homo sapiens

<400> SEQUENCE: 2
tccggggccc tcggggagc ggcgcctcct cctggttcca gcagctctgc gccgctcccc       60
acccaggccc gcgagaccag cgggacagtc cgcgccggga gaccaactgg gacgagccgc     120
gacccacgca ggcgcgctga ggccggggca ggggcgggcc cggctggcgc ggccggctgc     180
ggttggggct ggcgggggtg ggacgggcca agccgggcag gccggggtg gggcgctggc      240 gtttccgttg cttggatcag tctaggtgca gctgcggatc c                         281

<210> SEQ ID NO 3
<211> LENGTH: 436
<212> TYPE: DNA
<213> ORGANISM: Homo sapiens

<400> SEQUENCE: 3
ccgagccctg acagctcccc aggcccttc ccgcggcgcg aggacaagag gtctccgggg       60
ccctcggggg agcggcgcct cctcctggtt ccagcagctc tgcggccgct ccccacccag     120
gcccgcgaga ccagcgggac agtccgcgcc gcgggagacc aactgggacg agccgcgacc     180
cacgcaggcg cgctgaggcc ggggcagggg cgggcccgtg tggcgcggcc ggcctgcggt     240
tggggccctg gcggggtgg gacgggccaa gccgggcagg gccggggtgg ggccgctggc      300
gtttccgttg cttggatcag tctaggtgca gctgccggat ccttcagcgt ctgcatctcg     360
```

```
gcgtcgcccc gcgtaccgtc gcccggctct ccgccgctct cccgggggtt cggggcactt    420
gggtcccaca gtctgg                                                    436

<210> SEQ ID NO 4
<211> LENGTH: 289
<212> TYPE: DNA
<213> ORGANISM: Homo sapiens

<400> SEQUENCE: 4
tccggggccc tcgggggagc ggcgcctcct cctggttcca gcagctctgc ggccgctccc     60
cacccaggcc cgcgagacca gcgggacagt ccgcgccgcg ggagaccaac tgggacgagc    120
cgcgacccac gcaggcgcgc tgaggccggg gcagggcgg gcccggctgg cgcggccggc    180
ctgcggttgg ggccctggcg ggggtgggac gggccaagcc gggcagggcc ggggtggggc    240
cgctggcgtt tccgttgctt ggatcagtct aggtgcagct gccggatcc               289

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gtctaggtgc agctgccg                                                   18

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
gtctaggtgc agctgcca                                                   18

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
gaaccgggac acagaaac                                                   18

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8
ggccggcctg cggttgg                                                    17

<210> SEQ ID NO 9
<211> LENGTH: 17
<212> TYPE: DNA
<213> ORGANISM: Artificial Sequence
<220> FEATURE:
<223> OTHER INFORMATION: Primer
```

```
<400> SEQUENCE: 9
ggccggcctg cggttga                                                    17

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gttgtgggta aatccagcgc a                                               21

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
ccctggcggg ggtggga                                                    17

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
ccctggcggg ggtgggc                                                    17

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gttgtgggta aatccagcgc a                                               21

<210> SEQ ID NO 14
<211> LENGTH: 17
<212> TYPE: DNA
<213> ORGANISM: Artificial Sequence
<220> FEATURE:
<223> OTHER INFORMATION: Primer

<400> SEQUENCE: 14
ccgggcaggg ccggggt                                                    17

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15
ccgggcaggg ccggggc                                                    17

<210> SEQ ID NO 16
<211> LENGTH: 18
```

```
<212> TYPE: DNA
<213> ORGANISM: Artificial Sequence
<220> FEATURE:
<223> OTHER INFORMATION: Primer

<400> SEQUENCE: 16
gaaccgggac acagaaac                                                    18

<210> SEQ ID NO 17
<211> LENGTH: 12
<212> TYPE: DNA
<213> ORGANISM: Homo sapiens

<400> SEQUENCE: 17
tgcggttggg gc                                                          12

<210> SEQ ID NO 18
<211> LENGTH: 45
<212> TYPE: DNA
<213> ORGANISM: Homo sapiens

<400> SEQUENCE: 18 tggcggggt gggacgggcc aagccgggca gggccggggt ggggc                       45

<210> SEQ ID NO 19
<211> LENGTH: 41
<212> TYPE: DNA
<213> ORGANISM: Homo sapiens

<400> SEQUENCE: 19
gctggcgttt ccgttgcttg gatcagtcta ggtgcagctg c                          41

<210> SEQ ID NO 20
<211> LENGTH: 6
<212> TYPE: DNA
<213> ORGANISM: Homo sapiens

<400> SEQUENCE: 20 ggatcc                                                                  6

<210> SEQ ID NO 21
<211> LENGTH: 28
<212> TYPE: DNA
<213> ORGANISM: Artificial Sequence
<220> FEATURE:
<223> OTHER INFORMATION: Oligomer

<400> SEQUENCE: 21
ggttggggct ggcggggtg ggacgggc                                          28

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ccgagccctg gacagctccc ca                                               22

<210> SEQ ID NO 23
<211> LENGTH: 20
<212> TYPE: DNA
<213> ORGANISM: Artificial Sequence
<220> FEATURE:
```

```
<223> OTHER INFORMATION: Primer

<400> SEQUENCE: 23
ccagactgtg ggacccaagt                                              20
```